US012736070B2

United States Patent
(12) United States Patent
Kawano et al.

(10) Patent No.: US 12,736,070 B2
(45) Date of Patent: Sep. 15, 2026

(54) DETERMINATION APPARATUS, MOBILE OBJECT, COMPUTER-READABLE STORAGE MEDIUM, AND DETERMINATION METHOD

(71) Applicant: HONDA MOTOR CO., LTD., Tokyo (JP)

(72) Inventors: Shuji Kawano, Saitama (JP); Tsutomu Kamiyamaguchi, Saitama (JP); Yasuhito Takei, Saitama (JP)

(73) Assignee: HONDA MOTOR CO., LTD., Tokyo (JP)

( * ) Notice: Subject to any disclaimer, the term of this patent is extended or adjusted under 35 U.S.C. 154(b) by 769 days.

(21) Appl. No.: 18/190,145

(22) Filed: Mar. 27, 2023

(65) Prior Publication Data

US 2023/0392620 A1 Dec. 7, 2023

(30) Foreign Application Priority Data

Jun. 6, 2022 (JP) ................................ 2022-091375

(51) Int. Cl.
*F15B 19/00* (2006.01)
*G01N 33/28* (2006.01)
*G07C 5/08* (2006.01)

(52) U.S. Cl.
CPC ......... *F15B 19/00* (2013.01); *G01N 33/2888* (2013.01); *G07C 5/0808* (2013.01)

(58) Field of Classification Search
CPC .. F15B 19/00; F15B 19/005; F15B 2211/655; G01N 33/2888; G07C 5/0808
See application file for complete search history.

(56) References Cited

U.S. PATENT DOCUMENTS

| | | | | |
|---|---|---|---|---|
| 2002/0139331 A1* | 10/2002 | Takahashi | F02D 41/2493 | 123/90.17 |
| 2003/0005751 A1* | 1/2003 | Berndorfer | G01N 33/2888 | 73/54.01 |
| 2016/0133070 A1* | 5/2016 | Ikeda | G07C 5/0808 | 701/31.4 |
| 2023/0116404 A1* | 4/2023 | Miller | F04D 15/0066 | 417/12 |

FOREIGN PATENT DOCUMENTS

| | | | |
|---|---|---|---|
| DE | 102013204725 A1 * | 9/2014 | F02D 41/3082 |
| EP | 2341340 B1 * | 8/2015 | F16H 57/0405 |
| JP | S6397022 U * | 6/1988 | |
| JP | 2000230442 A | 8/2000 | |
| JP | 2016115426 A * | 6/2016 | B60L 58/40 |
| JP | 2022165463 A * | 11/2022 | |

* cited by examiner

*Primary Examiner* — Douglas Kay

(57) ABSTRACT

A determination apparatus configured to determine deterioration of a fluid to be used in circulation includes: a power index acquisition section configured to acquire information indicating a value of a power index, which is an index that represents a state of a pump for circulating the fluid and that is correlated with magnitude of power consumption of the pump; and a determination section configured to, based on the value of the power index acquired by the power index acquisition section, determine (i) whether the fluid has deteriorated, (ii) a degree of the deterioration of the fluid, and/or (iii) necessity of replacement of the fluid. The power index acquisition section may acquire the information indicating the value of the power index in each of one or more periods.

6 Claims, 14 Drawing Sheets

500

522 524

| TEMPERATURE RANGE OF FLUID | DETERMINATION CRITERION REGARDING POWER INDEX | |
|---|---|---|
| | TYPE | NUMERICAL RANGE AT NORMAL TIME |
| LESS THAN -10°C | POWER CONSUMPTION AMOUNT [Wh] | *** ~*** |
| -10°C OR MORE AND LESS THAN 0°C | | *** ~*** |
| 0°C OR MORE AND LESS THAN 10°C | | *** ~*** |
| ⋮ | | ⋮ |
| 90°C OR MORE AND LESS THAN 100°C | | *** ~*** |
| 100°C OR MORE | | *** ~*** |

| TEMPERATURE RANGE OF FLUID | OUTSIDE AIR TEMPERATURE RANGE | DETERMINATION CRITERION REGARDING POWER INDEX | |
|---|---|---|---|
| | | TYPE | NUMERICAL RANGE AT NORMAL TIME |
| LESS THAN -10°C | LESS THAN -10°C | POWER CONSUMPTION AMOUNT [Wh] | *** ~*** |
| ⋮ | | | ⋮ |
| 100°C OR MORE | | | *** ~*** |
| ⋮ | ⋮ | | ⋮ |
| LESS THAN -10°C | 40°C OR MORE | | *** ~*** |
| ⋮ | | | ⋮ |
| 100°C OR MORE | | | *** ~*** |

| IDENTIFICATION INFORMATION OF DC | IDENTIFICATION INFORMATION OF SAMPLING PERIOD (COMMENCEMENT) | MEASUREMENT TIME | MEASUREMENT VALUE | | | |
|---|---|---|---|---|---|---|
| | | | FLUID TEMPERATURE | ENVIRONMENT TEMPERATURE | ROTATION SPEED | TORQUE |
| DC001 | SP001 (2022/5/14 22:00:00) | 22:00:00 | 40°C | *** | 100 rpm | *** |
| | | ⋮ | ⋮ | ⋮ | ⋮ | ⋮ |
| | | 22:00:30 | 40°C | *** | 100 rpm | *** |
| | SP002 (2022/5/14 22:12:20) | 22:12:20 | 80°C | *** | 100 rpm | *** |
| | | ⋮ | ⋮ | ⋮ | ⋮ | ⋮ |
| | | 22:12:50 | 80°C | *** | 100 rpm | *** |
| | ⋮ | ⋮ | ⋮ | ⋮ | ⋮ | ⋮ |

| IDENTIFICATION INFORMATION OF DC (1022) | IDENTIFICATION INFORMATION OF SAMPLING PERIOD (1024) | MEASUREMENT RESULT OF POWER INDEX (1032) | | DETERMINATION RESULT OF POWER INDEX (1034) |
|---|---|---|---|---|
| | | TYPE | VALUE | |
| DC001 | SP001 | MEAN VALUE OF TORQUE AT REFERENCE ROTATION SPEED | *** | OK |
| | SP002 | | *** | Fail |
| | ⋮ | | ⋮ | ⋮ |
| ⋮ | ⋮ | ⋮ | ⋮ | ⋮ |

DETERMINATION APPARATUS, MOBILE OBJECT, COMPUTER-READABLE STORAGE MEDIUM, AND DETERMINATION METHOD

The contents of the following Japanese application are incorporated herein by reference. NO. 2022-091375 filed in JP on Jun. 6, 2022.

BACKGROUND

1. Technical Field

The present invention relates to a determination apparatus, a mobile object, a computer-readable storage medium, and a determination method.

2. Related Art

Patent Document 1 discloses that, in a power transmission device having an electric hydraulic pressure generating means, deterioration of that electric hydraulic pressure generating means is detected.

PRIOR ART DOCUMENT

Patent Document

Patent Document 1: Japanese Patent Application Publication No. 2000-230442

BRIEF DESCRIPTION OF THE DRAWINGS

FIG. 5 schematically shows one example of a data structure of a determination criterion regarding power index 500.

FIG. 6 schematically shows one example of a data structure of a determination criterion regarding power index 600.

FIG. 9 schematically shows one example of a data structure of a measurement data 900.

FIG. 10 schematically shows one example of a data structure of a determination result of power index 1000.

DESCRIPTION OF EXEMPLARY EMBODIMENTS

Hereinafter, the present invention will be described through embodiments of the invention, but the following embodiments do not limit the invention according to the claims. In addition, not all combinations of features described in the embodiments are essential to the solution of the invention.

(Overview of Management System 100)

Figure 1:
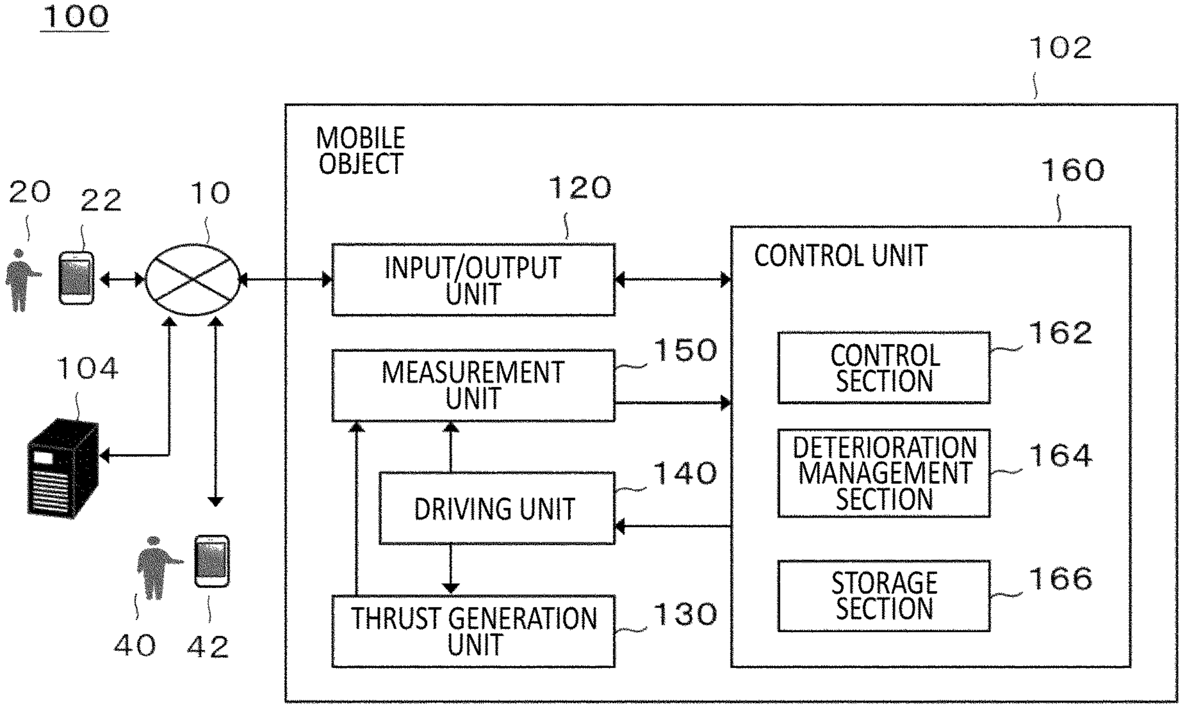
FIG. 1 schematically shows one example of a system configuration of the management system 100.

FIG. 1 schematically shows one example of a system configuration of the management system 100. In the present embodiment, the management system 100 includes one or more mobile objects 102 and a management server 104, for example. In the present embodiment, the mobile object 102 includes an input/output unit 120, a thrust generation unit 130, a driving unit 140, a measurement unit 150, and a control unit 160, for example. In the present embodiment, the control unit 160 has a control section 162, a deterioration management section 164, and a storage section 166.

In the present embodiment, the one or more mobile objects 102 and the management server 104 can transmit and receive information to and from each other via a communication network 10. For example, each of the one or more mobile objects 102 can transmit and receive a variety of information to and from the management server 104 via the communication network 10 including a mobile communication network and/or a wireless communication network. In the present embodiment, the input/output unit 120, the thrust generation unit 130, the driving unit 140, the measurement unit 150, and the control unit 160 are configured to be capable of transmitting and receiving information to and from one another, for example.

The one or more mobile objects 102 and/or the management server 104 can transmit and receive a variety of information to and from a communication terminal 22 to be utilized by a user 20, via the communication network 10. Similarly, the one or more mobile objects 102 and/or the management server 104 can transmit and receive a variety of information to and from a communication terminal 42 to be utilized by a maintenance company 40, via the communication network 10.

The user 20 may be a utilizer of the mobile object 102, may be an owner of the mobile object 102, or may be an operation manager managing operation of the mobile object 102. The maintenance company 40 may be an operator executing maintenance of the mobile object 102, may be an operator (for example, a seller) accepting a request for the maintenance of the mobile object 102, or may be an operator (for example, a manufacturer) managing the maintenance of the mobile object 102.

The communication terminal 22 and the communication terminal 42 may be any equipment capable of transmitting and receiving information to and from another information processing apparatus via the communication network 10, details of which are not particularly limited. Examples of the communication terminal 22 and/or the communication terminal 42 include a personal computer, a mobile terminal, and the like. Examples of the mobile terminal include a mobile phone, a smartphone, a PDA, a tablet, a notebook computer or a laptop computer, a wearable computer, and the like.

(Overview of Determination Processing in Management System 100)

In the present embodiment, a technique for determining deterioration of a fluid to be used in circulation inside the mobile object 102 is described in detail, by taking as an example a case where the deterioration management section 164 is mounted on the mobile object 102. However, note that the deterioration management section 164 is not limited to the present embodiment. In another embodiment, the deterioration management section 164 may be arranged inside the management server 104, for example. In yet another embodiment, the deterioration management section 164 may be arranged inside the communication terminal 22 and/or the communication terminal 42. In these embodiments, the deterioration management section 164 may acquire a variety of information used for the determination processing of the deterioration of the fluid from the mobile object 102 via the communication network 10.

In the mobile object 102, a fluid is supplied to a machine component for the purpose of lubricating and/or cooling that machine component, for example. The above fluid is used in circulation inside the mobile object 102. When the above fluid deteriorates, its lubricating performance and/or cooling performance decrease. For example, due to pressure or shear stress applied to a fluid while that fluid is being used in circulation, a change in a temperature of a fluid while that fluid is being used in circulation, or the like, viscosity of that fluid decreases. In addition, fine powder generated by wear of the machine component is mixed into the above fluid. The decreased lubricating performance and/or cooling performance of the above fluid can cause damage or failure of the machine component. Therefore, the above fluid is desirably replaced at appropriate timing.

As a technique for presuming the deterioration of the fluid described above, it is conceivable to presume that deterioration of the fluid based on a movement distance of the mobile object 102, an operating hour of the mobile object 102, or the like. However, as mentioned above, the deterioration of the fluid described above is caused by heat and pressure applied to the fluid. Therefore, a degree of the deterioration of the fluid described above greatly varies depending on how the mobile object 102 is used. For example, degrees of the deterioration of the fluid described above greatly differ between a case where the mobile object 102 is used in a general household and a case where the mobile object 102 is used in business such as transport business or delivery business, even if movement distances of the mobile object 102 or operating hours of the mobile object 102 are the same.

As another technique for presuming the deterioration of the fluid described above, it is conceivable to acquire and save for each user 20 or mobile object 102 a history of a load applied to the fluid and to presume that deterioration of the fluid based on that history of the load. However, the above technique is complicated and is not cost effective.

The inventors of the present invention found that there was a correlation between power or power consumption of a motor driving a pump for circulating the above fluid (which may be simply referred to as power of a pump, power consumption of a pump, or the like, with reference to the motor being omitted), and a state of that fluid. Note that the power (W) of the motor driving the pump is derived as a product of torque (N·m) of that motor and rotation speed (rpm) of that motor. The power consumption (W) of the motor driving the pump may be derived based on the power (W) of the above motor and efficiency (%) of that motor. In addition, measuring the rotation speed and the torque of the motor at the same operational point allows net power consumption (which may be simply referred to as power consumption) including that efficiency of the motor to be derived as a product of a measurement value of the rotation speed and a measurement value of the torque. Therefore, the inventors of the present invention conceived of presuming the state of the fluid described above, based on a measurement value of the torque, the rotation speed, the power consumption, or the like of the motor.

In general, when viscosity of a fluid decreases, required power for a pump decreases. On the other hand, when a solid is mixed into the fluid, the required power for the pump increases. In addition, the viscosity of the fluid greatly varies depending on a temperature of the fluid. Therefore, the inventors of the present invention performed a test of circulating, in a flow channel including a gearbox by using a pump, each of a new lubricant agent and a lubricant agent that has deteriorated to the extent that replacement was required due to a high-temperature and high-load acceleration test. During a test period having a predetermined length, rotation speed and torque of a motor driving the above pump were measured. In addition, as the power consumption of the motor described above, net power consumption of that motor was calculated based on the measurement values of the rotation speed and the torque described above.

The inventors of the present invention repeated the above test by variously changing a temperature of the new lubricant agent and a temperature of the deteriorated lubricant agent. In a plurality of tests, operating conditions of the gearbox and lengths of the test period were the same. As a result, the inventors of the present invention found that, if deterioration states of the lubricant agent were the same, the power consumption of the motor driving the pump monotonically decreased as the temperature of the fluid increased. In addition, they found that, if temperatures were the same, the power consumption of the motor driving the pump monotonically decreased as the deterioration progressed. This means that, even in consideration of an influence on the power consumption due to mixing of wear powder to be generated in the gearbox into the lubricant agent, decrease in viscosity of the lubricant agent caused by the deterioration of the lubricant agent has a large influence on the power consumption. For example, shear stress to be applied to the lubricant agent by a constituent component of the gearbox destroys a polymer contained in the lubricant agent, thereby decreasing the viscosity of the lubricant agent.

Based on the above knowledge, the inventors of the present invention found that a deterioration state of that fluid could be presumed based on the power or the power consumption of the motor driving the pump for circulating the fluid. In addition, the inventors of the present invention found that the deterioration state of the fluid could be presumed with adequate accuracy by appropriately dividing a temperature range into a plurality of temperature ranges and determining the deterioration state of the fluid for each of the temperature ranges.

As mentioned above, it is desired to reduce $CO_2$ emissions during use or a manufacturing process of equipment and to improve energy efficiency. According to the present embodiment, for example, it is possible to presume appropriately timing of replacement of the fluid to be used for lubricating and/or cooling the machine component mounted on the equipment. This improves efficiency of the machine component. As a result, the $CO_2$ emissions during use of the equipment are reduced. In addition, a use period of the machine component mounted on the equipment is lengthened. As a result, the $CO_2$ emissions in the manufacturing process of the equipment are reduced.

(Overview of Each Unit Related to Management System 100)

In the present embodiment, the communication network 10 may be a transmission path of wired communication, may be a transmission path of wireless communication, or may be a combination of the transmission path of the wired communication and the transmission path of the wireless communication. The communication network 10 may include a wireless packet communication network, the Internet, a P2P network, a dedicated line, a VPN, a power line communication line, a vehicle-to-vehicle communication line, inter-road communication line, or the like.

As mentioned above, the communication network 10: (i) may include a mobile communication network such as a mobile phone line network; and (ii) may include a wireless communication network such as a wireless MAN (for example, WiMAX (registered trademark)), a wireless LAN (for example, WiFi (registered trademark)), Bluetooth (registered trademark), Zigbee (registered trademark) or NFC (Near Field Communication). The wireless LAN, Bluetooth (registered trademark), Zigbee (registered trademark), and NFC may be examples of short-range wireless communication.

(Overview of Mobile Object 102)

In the present embodiment, the mobile object 102 moves with a person or an object mounted thereon, for example. The mobile object 102 may be moved by control of the user 20 boarding on the mobile object 102, may be moved by remote control, or may be autonomously moved. Each unit of the mobile object 102 will be described later in detail.

Examples of the mobile object 102 include a vehicle, a flight vehicle, a marine vessel, and the like. Examples of the vehicle include an automobile, a two-wheeled motor vehicle, a bicycle, a stand-up riding vehicle having a power unit, a work machine, a train, and the like. Examples of the automobile include an electric automobile, a fuel cell vehicle (FCV), a hybrid car, a small commuter, an electrically driven cart, and the like. Examples of the two-wheeled motor vehicle include a motorcycle, a tricycle, and the like. The bicycle may be a motorized bicycle. The motorized bicycle may be an electrically driven bicycle or may be an electrically assisted bicycle. Examples of the work machine include a forklift, a cultivator, a lawn trimmer, and the like. Examples of the flight vehicle include an airplane, an airship or a balloon, an aerostat, a helicopter, a drone, and the like. Examples of the marine vessel include a ship, a hovercraft, a water bike, a submarine ship, a submarine boat, an underwater scooter, and the like.

(Overview of Management Server 104)

In the present embodiment, the management server 104 manages information on each of the one or more mobile objects 102. For example, the management server 104 manages a type or model, a position, a state, or the like, for each of the one or more mobile objects 102. The management server 104 may acquire, from each of the one or more mobile objects 102, information indicating a state of that mobile object via the communication network 10, and store that information in association with identification information of each mobile object.

Examples of a state of the mobile object 102 include a movement status of the mobile object 102, a start status of a constituent component of the mobile object 102, a deterioration status of the constituent component of the mobile object 102, and the like. Examples of the movement status of the mobile object 102 include whether the mobile object 102 has stopped, velocity of the mobile object 102, angular velocity of the mobile object 102, and the like. For example, if a state where movement velocity of the mobile object 102 is 0 km/h continues for a predetermined period of time, it is determined that the mobile object 102 has stopped. Examples of the start status of the constituent component include whether that constituent component has been started, presence or absence of an instruction to start that constituent component, a type of that instruction, and the like. Examples of the deterioration status of the constituent component include whether that constituent component has deteriorated, a degree of deterioration of that constituent component, and/or necessity of replacement of that constituent component, and the like.

The above constituent component includes the fluid to be used in circulation inside the mobile object 102 and/or the pump for circulating that fluid, for example. Examples of the above fluid include a lubricant agent.

The management server 104 may manage information on one or more users 20 utilizing each of the one or more mobile objects 102. For example, the management server 104 may manage, for each of the one or more users 20, an address for that user to receive information.

The management server 104 may manage information on one or more maintenance companies 40 capable of maintaining each of the one or more mobile objects 102 or one or more maintenance companies 40 capable of accepting maintenance of each of the one or more mobile objects 102. The management server 104 may manage, for each of the one or more mobile objects 102, identification information of that mobile object and an address for the above one or more maintenance companies 40 to receive information in association with each other.

If a deterioration status of a constituent component of a specific mobile object 102 meets a predetermined condition, the management server 104 may notify the user 20 utilizing that specific mobile object 102 of a state of that constituent component. If the deterioration status of the constituent component of the specific mobile object 102 meets the predetermined condition, the management server 104 may notify the maintenance company 40 associated with that specific mobile object 102 of identification information of that specific mobile object 102 and the state of that constituent component. Examples of the predetermined condition include a case where it is determined that a specific constituent component has deteriorated, a case where a degree of deterioration of the specific constituent component has exceeded a predetermined criterion, a case where it is determined that replacement of the specific constituent component is necessary, and the like.

(Overview of Each Unit of Mobile Object 102)

In the present embodiment, the input/output unit 120 accepts input of operation or an instruction from the user 20, for example. The input/output unit 120 may acquire information indicating a type of operation instructed by the user 20 to the mobile object 102 and an operation amount. The input/output unit 120 presents a variety of information, for example. The input/output unit 120 may output a variety of information on the state of the mobile object 102. The input/output unit 120 may have a communication function. The input/output unit 120 may transmit and receive information to and from the communication terminal 22, the communication terminal 42, and/or the management server 104 via the communication network 10. The input/output unit 120 operates based on an instruction from the control unit 160, for example.

The input/output unit 120 includes various input apparatuses, various output apparatuses, and/or various communication apparatuses, for example. Examples of the input apparatus include a handle, an accelerator, a brake, a shift lever, a direction indicator, and the like. Other examples of the input apparatus include a keyboard, a pointing device, a touch panel, a camera, a microphone, a speech input system, a gesture input system, and the like. Examples of the output apparatus include a display apparatus, a speaker, and the like. Examples of the display apparatus include a display, a projector, and the like. The communication apparatus may be any equipment that can be connected to the communication network 10, details of which are not limited.

In the present embodiment, the thrust generation unit 130 generates thrust of the mobile object 102, for example. The thrust generation unit 130 may generate the thrust of the mobile object 102 by utilizing driving force outputted by the driving unit 140. Examples of the thrust generation unit 130 include a wheel, a propeller, and the like.

In the present embodiment, the driving unit 140 outputs the driving force for moving the mobile object 102, for example. The driving unit 140 may output braking force for braking the mobile object 102. The driving unit 140 operates based on an instruction from the control unit 160, for example. The driving unit 140 will be described later in detail.

In the present embodiment, the measurement unit 150 measures various physical amounts indicating the state of the mobile object 102. The measurement unit 150 may measure various physical amounts indicating a state of the driving unit 140. The measurement unit 150 may output, to the control unit 160, information indicating a measurement result.

The measurement unit 150 may include various sensors. Examples of the above sensors include a velocity sensor, an angular velocity sensor, a current sensor, a voltage sensor, a rotation sensor (which may be referred to as a resolver), a temperature sensor, a pressure sensor, and the like. The temperature sensor measures an oil temperature, a water temperature, an air temperature, a surface temperature of the component, an internal temperature of the component, or the like, for example. The measurement unit 150 will be described later in detail.

In the present embodiment, the control unit 160 controls the mobile object 102, for example. In one embodiment, the control unit 160 manages a state of each unit of the mobile object 102. For example, the control unit 160 acquires a measurement result indicating the state of each unit of the mobile object 102 from the measurement unit 150. The control unit 160 may diagnose the state of each unit of the mobile object 102. In another embodiment, the control unit 160 may control operation of each unit of the mobile object 102. For example, the control unit 160 controls operation of the driving unit 140.

In the present embodiment, the control section 162 controls the operation of each unit of the mobile object 102, for example. The control section 162 may acquire the measurement result indicating the state of each unit of the mobile object 102 from the measurement unit 150. The control section 162 may control the operation of each unit of the mobile object 102 based on the above measurement result. The control section 162 controls the operation of the driving unit 140, for example.

In the present embodiment, the deterioration management section 164 manages states of at least some components of a plurality of components (which may be referred to as constituent components) constituting the mobile object 102. The deterioration management section 164 manages states of deterioration of the above components. Specifically, the deterioration management section 164 manages a state of the deterioration of the fluid to be used in circulation inside the mobile object 102. The deterioration management section 164 determines that state of the deterioration of the fluid based on a state of the pump for circulating the above fluid. The deterioration management section 164 will be described later in detail.

In the present embodiment, the storage section 166 memorizes (which may be referred to as stores) a variety of information. In one embodiment, the storage section 166 stores a variety of information used for information processing in the mobile object 102. In another embodiment, the storage section 166 stores a variety of information generated through the information processing in the mobile object 102. The storage section 166 will be described later in detail.

(Specific Configuration of Each Unit of the Mobile Object 102)

Each unit of the mobile object 102 may be realized by hardware, may be realized by software, or may be realized by hardware and software. Each unit of the mobile object 102 may be, at least partially, realized by a personal computer or mobile terminal. For example, the personal computer or the mobile terminal may be utilized as a user interface of the mobile object 102. Examples of the mobile terminal include a mobile phone, a smartphone, a PDA, a tablet, a notebook computer or a laptop computer, a wearable computer, and the like.

If at least some of constituent elements constituting the mobile object 102 are realized by software, the constituent elements realized by that software may be realized by activating, in an information processing apparatus having a general configuration, a program stipulating operations regarding those constituent elements. The above information processing apparatus includes, for example, (i) a data processing apparatus having various processors (as a processor, a CPU, a GPU, or the like is exemplified), a ROM, a RAM, a communication interface, or the like, and (ii) a storage apparatus such as a memory or an HDD (including an external storage apparatus). The above information processing apparatus may include (iii) an input apparatus such as a keyboard, a touch panel, a camera, a microphone, various sensors, or a GPS receiver, or may include (iv) an output apparatus such as a display apparatus, a speaker, or a vibration apparatus.

In the above information processing apparatus, the data processing apparatus or the storage apparatus described above may store a program. The information processing described in the above program functions as a specific means realized by cooperation between software related to that program and various hardware resources constituting at least part of the mobile object 102, when that program is read into a computer, for example. Then, the above specific means realizes calculation or processing of information corresponding to an intended use of the computer in the present embodiment, thereby constructing the mobile object 102 or a part thereof corresponding to that intended use.

The above program may be stored on a computer-readable medium. The above program may be stored in a non-transitory computer-readable storage medium. The above program may be stored in a computer-readable medium such as a CD-ROM, a DVD-ROM, a memory, a hard disk, or may be stored in a storage apparatus connected to a network. The above program may be installed from the computer-readable medium or the storage apparatus connected to the network onto a computer constituting the at least part of the mobile object 102.

When the above program is performed, the computer may function as at least part of each unit of the mobile object 102. When the above program is performed, the computer may perform an information processing method in the at least part of the mobile object 102.

The program for causing the computer to function as the at least part of the mobile object 102 includes a module stipulating operations of the at least part of the mobile object 102, for example. When the program or the module described above is performed, the program or the module described above instructs the data processing apparatus, the input apparatus, the output apparatus, the storage apparatus, or the like, to cause the computer to function as the at least part of the mobile object 102, or to cause the computer to perform the information processing method in the at least part of the mobile object 102.

The above information processing method may be a determination method for determining the deterioration of the fluid to be used in circulation. The above determination method has acquiring a power index, which is an index that represents the state of the pump for circulating the fluid and that is correlated with magnitude of the power consumption of the pump, by acquiring information indicating a value of the power index, for example. The above determination method has determining (i) whether the fluid has deteriorated, (ii) a degree of the deterioration of the fluid, and/or (iii) necessity of replacement of the fluid based on the value of the power index acquired in the acquiring the power index, for example. Each step of the above determination method may be performed by the computer.

The management system 100 may be one example of a determination apparatus. The mobile object 102 may be one example of a determination apparatus. If the deterioration management section 164 is arranged in the management server 104, the management server 104 may be one example of a determination apparatus. The driving unit 140 may be one example of a machine component. The measurement unit 150 may be one example of a fluid temperature acquisition section, an environment temperature acquisition section, and/or a power index acquisition section. The control unit 160 may be one example of a determination apparatus. The control section 162 may be one example of a determination apparatus. The fluid to be used in circulation inside the mobile object 102 may be one example of a fluid. The thrust generation unit 130 may be one example of a thrust generation section generating thrust of a mobile object.

(Overview of Driving Unit 140)

Figure 2:
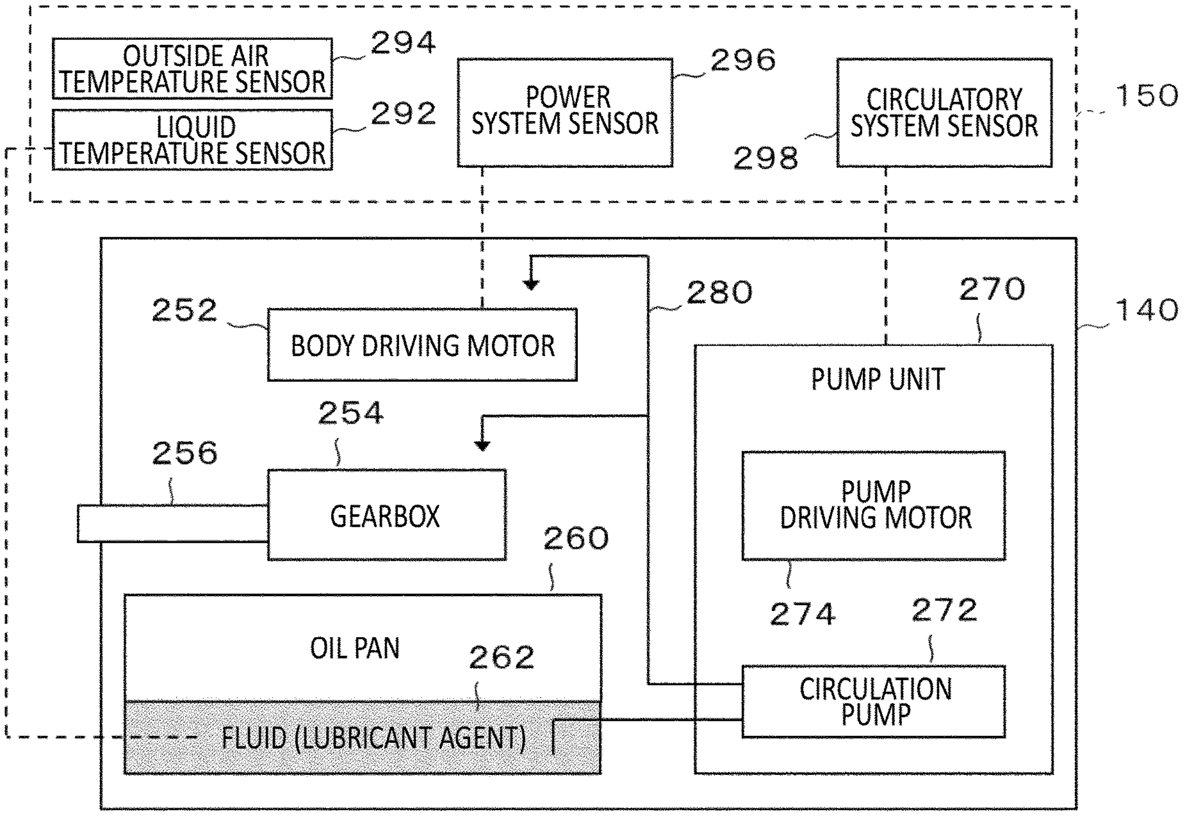
FIG. 2 schematically shows one example of an internal configuration of a driving unit 140.

FIG. 2 schematically shows one example of an internal configuration of the driving unit 140 together with one example of an internal configuration of the measurement unit 150. In the present embodiment, the driving unit 140 includes a body driving motor 252, a gearbox 254, a shaft 256, an oil pan 260, a fluid 262, a pump unit 270, and a flow channel 280, for example. In the present embodiment, the pump unit 270 has a circulation pump 272 and a pump driving motor 274, for example. In the present embodiment, the measurement unit 150 includes a liquid temperature sensor 292, an outside air temperature sensor 294, a power system sensor 296, and a circulatory system sensor 298, for example.

In the present embodiment, the body driving motor 252 generates power. The body driving motor 252 generates power for driving the mobile object 102, for example. In the present embodiment, the gearbox 254 transmits the power generated by the body driving motor 252 to the shaft 256. This allows the gearbox 254 to transmit the power generated by the body driving motor 252 to the thrust generation unit 130 and to drive the mobile object 102. The gearbox 254 is composed of one or more machine components. The gearbox 254 includes a rotary component such as a bearing or a gear, for example. In the present embodiment, the shaft 256 transmits the power generated by the body driving motor 252 to the thrust generation unit 130. This allows the shaft 256 to drive the mobile object 102.

In the present embodiment, the oil pan 260 reserves the fluid 262. In the present embodiment, the fluid 262 is used in circulation. The fluid 262 contains, as a principal component, a liquid whose viscosity at a predetermined temperature or in a predetermined temperature range decreases as deterioration of the liquid progresses, for example. The fluid 262 contains, as a principal component, a lubricant agent to be used for lubricating the body driving motor 252, the gearbox 254, and/or the shaft 256, for example. The fluid 262 may be a liquid containing a lubricant agent as a principal component.

In the present embodiment, the pump unit 270 consumes power to transport the fluid 262. In the present embodiment, the circulation pump 272, for example, sucks the fluid 262 reserved in the oil pan 260, and supplies the above fluid 262 to the gearbox 254 and/or the shaft 256 via the flow channel 280. The above fluid 262 is used for lubricating and/or cooling the body driving motor 252, the gearbox 254, and/or the shaft 256, and is then reserved in the oil pan 260 again. This allows the fluid 262 to be used in circulation by the pump unit 270.

In the present embodiment, the pump driving motor 274 consumes power to drive the circulation pump 272. The pump driving motor 274 may output, to the circulatory system sensor 298, information indicating a value of an index (which may be referred to as a power index) correlated with magnitude of power consumption of the pump driving motor 274.

Examples of the power index include at least one of rotation speed (r/min), torque (N·m), or power consumption (W) of the pump driving motor 274. The power index may be the rotation speed and the torque of the pump driving motor 274, or may be the power consumption of the pump driving motor 274. If the rotation speed of the pump driving motor 274 is known, the power index may be the torque of the pump driving motor 274.

The power index may be at least one of power consumption amount (Wh) of the pump driving motor 274 in a period having a specific length, a statistic amount of the power consumption (W) of the pump driving motor 274 in that period, a statistic amount of the rotation speed (r/min) of the pump driving motor 274 in that period, or a statistic amount of the torque (N·m) of the pump driving motor 274 in that period. The above statistic amount may be a fundamental statistic amount representing a center of distribution of a plurality of measurement values measured in the above period, may be a statistic amount representing expansion of that distribution, or may be a fundamental statistic amount representing a profile of that distribution. Examples of the above statistic amount include at least one of (i) a mean value, (ii) a median value, (iii) a mode value, (iv) variance, (v) unbiased variance, (vi) a standard deviation, (vii) a variation coefficient, (viii) difference between a maximum value and a minimum value, (ix) skewness, or (x) kurtosis.

The power index may be the above power consumption amount, may be a statistic amount of the above power consumption, or may be a statistic amount of the above rotation speed and a statistic amount of the above torque. If the rotation speed of the pump driving motor 274 in the above period is a predetermined value or falls within a predetermined numerical range, or if the rotation speed of the pump driving motor 274 in the above period is known, the power index may be at least one of the above power consumption amount, the statistic amount of the power consumption described above, or the statistic amount of the torque described above. If the rotation speed of the pump driving motor 274 in the above period is the predetermined value or falls within the predetermined numerical range, or if the rotation speed of the pump driving motor 274 in the above period is known, the power index may be the statistic amount of the torque described above.

The power consumption of the pump driving motor 274 may be used as an index representing a state of the pump unit 270 or the circulation pump 272. The power consumption of the pump driving motor 274 may be used as an index representing power consumption of the pump unit 270 or the circulation pump 272.

In the present embodiment, the liquid temperature sensor 292 measures a temperature of the fluid 262. The liquid temperature sensor 292 may measure the temperature of the fluid 262 reserved in the oil pan 260. The liquid temperature sensor 292 may output, to the control unit 160, information indicating time and information indicating the temperature of the fluid 262 at that time in association with each other. As a result, the information indicating the temperature of the fluid 262 is acquired.

In the present embodiment, the outside air temperature sensor 294 measures an outside air temperature of the mobile object 102. The outside air temperature sensor 294 may output, to the control unit 160, the information indicating the time and information indicating the outside air temperature at that time in association with each other. As a result, the information indicating the outside air temperature is acquired.

For example, if the temperature of the fluid 262 increases, difference between the temperature of the fluid 262 and the outside air temperature is utilized to cool the fluid 262. As mentioned above, the viscosity of the fluid 262 is affected by the temperature of the fluid 262. Therefore, the outside air temperature may affect the viscosity of the fluid 262.

In the present embodiment, the power system sensor 296 measures various physical amounts regarding a movement status of the mobile object 102. For example, the power system sensor 296 measures at least one of velocity, angular velocity, a movement direction, or a movement distance of the mobile object 102. The power system sensor 296 may measure at least one of rotation speed, torque, or power consumption of the body driving motor 252. The power system sensor 296 may measure at least one of movement velocity of the mobile object 102, a movement distance from a position where the user 20 of the mobile object 102 started the mobile object 102, or elapsed time from a time point where the user 20 of the mobile object 102 started the mobile object 102. The power system sensor 296 may output, to the control unit 160, the information indicating the time and information indicating the movement status of the mobile object 102 at that time in association with each other. As a result, the information indicating the movement status of the mobile object 102 is acquired.

In the present embodiment, the circulatory system sensor 298 acquires information indicating a value of the above power index from the pump unit 270. The circulatory system sensor 298 may measure at least one of the rotation speed, the torque, or the power consumption of the pump driving motor 274, and generate, based on that measurement value, the information indicating the value of the power index described above. The circulatory system sensor 298 may output, to the control unit 160, information indicating time or a period and information indicating the value of the power index at that time or in that period in association with each other. As a result, the information indicating the value of the power index is acquired. The information indicating the period may be identification information of that period, may be information indicating commencement of that period, or may be information indicating termination of that period.

The body driving motor 252 may be one example of a machine component. The gearbox 254 may be one example of a machine component. The shaft 256 may be one example of a machine component. The fluid 262 may be one example of a fluid to be used in circulation. The pump unit 270 may be one example of a pump. The circulation pump 272 may be one example of a pump. The power consumption of the pump unit 270 may be one example of power consumption of a pump. The power consumption of the pump driving motor 274 may be one example of power consumption of a pump. The liquid temperature sensor 292 may be one example of a fluid temperature acquisition section. The outside air temperature sensor 294 may be one example of an environment temperature acquisition section. The circulatory system sensor 298 may be one example of a power index acquisition section. The outside air may be one example of an environment in which a fluid is used.

The body driving motor 252 may be one example of a power generation section for generating power. The shaft 256 may be one example of a power transmission section for transmitting power generated by a power generation section to a thrust generation section.

Figure 3:
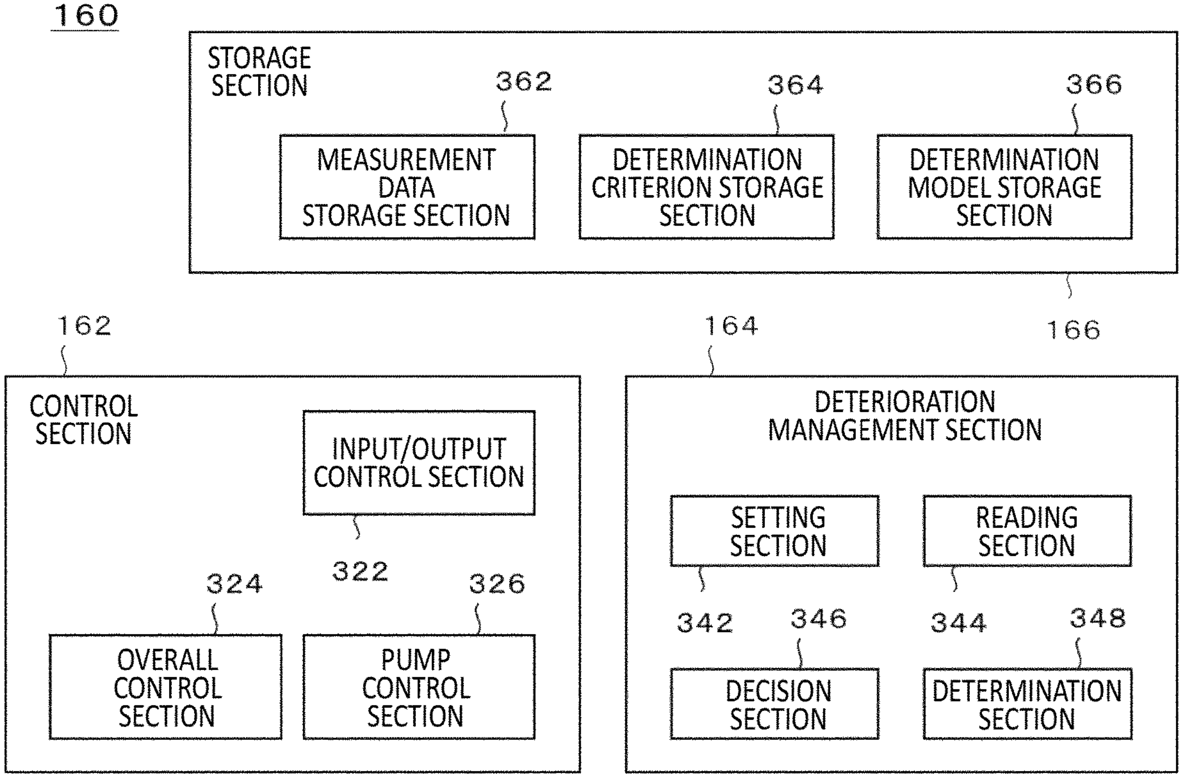
FIG. 3 schematically shows one example of an internal configuration of a control unit 160.

FIG. 3 schematically shows one example of an internal configuration of the control unit 160. In the present embodiment, the control section 162 includes an input/output control section 322, an overall control section 324, and a pump control section 326. In the present embodiment, the deterioration management section 164 includes a setting section 342, a reading section 344, a decision section 346, and a determination section 348. The storage section 166 includes a measurement data storage section 362, a determination criterion storage section 364, and a determination model storage section 366.

The input/output control section 322 controls input/output between the mobile object 102 and an outside of the mobile object 102. The input/output control section 322 acquires information indicating a content of an instruction of the user 20 outputted by the input/output unit 120, for example. The input/output control section 322 outputs, to the input/output unit 120, the information to be presented from the input/output unit 120 to the user 20, for example. The input/output control section 322 may control communication between the control unit 160, and the communication terminal 22, the communication terminal 42, and/or management server 104.

In the present embodiment, the overall control section 324 controls overall operation of the mobile object 102. For example, the overall control section 324 controls operation of each unit related to driving of the mobile object 102.

In the present embodiment, the pump control section 326 controls operation of the pump unit 270. The pump control section 326 may control rotation speed and/or torque of the pump driving motor 274. The pump control section 326 may decide timing to start the pump unit 270. The pump control section 326 may start the pump unit 270 by outputting an instruction to start the pump unit 270 to the pump unit 270. The above instruction may include information indicating target values for rotation speed and/or torque.

Examples of a type of the above instruction include (i) an instruction to start the pump unit 270 for the purpose of determining deterioration of the fluid 262, (ii) an instruction to start the pump unit 270 for the purpose of lubricating and/or cooling the body driving motor 252, the gearbox 254, and/or the shaft 256, and the like. An operation mode to start the pump unit 270 for the purpose of determining the deterioration of the fluid 262 is referred to as an oil deterioration determination mode, for example. An operation mode to start the pump unit 270 for the purpose of lubricating and/or cooling the body driving motor 252, the gearbox 254, and/or the shaft 256 is referred to as a cooling/lubricating mode, for example.

In the present embodiment, the setting section 342 decides various setting contents regarding determination processing of the deterioration (which may be referred to as deterioration determination) of the fluid 262 in the deterioration management section 164, for example. The setting section 342 may decide the various setting contents based on an instruction from the user 20 received via the input/output unit 120.

The setting section 342 may automatically change specific setting contents according to a predetermined algorithm. For example, the setting section 342 changes, based on (i) an operating frequency of the mobile object 102 or the driving unit 140, or (ii) a determination result of deterioration determination in another mobile object 102 or driving unit 140 of the same type, setting contents associated in advance with that operating frequency or that determination result. The operating frequency of the mobile object 102 or the driving unit 140 may be a frequency with which the user 20 uses these pieces of equipment. Examples of the another mobile object 102 or driving unit 140 of the same type include a mobile object 102 or a driving unit 140 of the same or similar type. Examples of the above type include a model, a model number, a lot, and the like.

In one embodiment, the setting section 342 decides setting contents regarding a period in which the deterioration determination is to take place (which may be referred to as a determination period). Examples of the determination period include a driving cycle, a period having a predetermined length, and the like. The setting section 342 may automatically change setting contents regarding the determination period according to a predetermined algorithm. The setting section 342 may decide and/or change the setting contents regarding the determination period based on (i) the operating frequency of the mobile object 102 or the driving unit 140, or (ii) the determination result of the deterioration determination in the another mobile object 102 or driving unit 140 of the same type.

For example, if the above operating frequency is smaller than a predetermined value, the setting section 342 decides the setting contents regarding the determination period described above such that the deterioration determination is executed for each driving cycle, and if necessary changes those setting contents. For example, if deterioration of a fluid is detected in the another mobile object 102 or driving unit 140 of the same type, the setting section 342 acquires information on that deterioration from that another mobile object 102, that another driving unit 140, or the management server 104. The setting section 342 decides the setting contents regarding the determination period described above such that execution time of a next deterioration determination is moved earlier and/or such that an execution frequency of the deterioration determination increases, and if necessary changes those setting contents. The setting section 342 may decide and/or change the setting contents regarding the execution time of the next deterioration determination and/or the execution frequency of the deterioration determination.

In another embodiment, the setting section 342 decides setting contents regarding a type of a power index to be used in the deterioration determination. The setting section 342 may automatically change the setting contents regarding the type of the power index described above according to a predetermined algorithm. The setting section 342 may decide and/or change the setting contents regarding the type of the power index described above, based on (i) the operating frequency of the mobile object 102 or the driving unit 140, or (ii) the determination result of the deterioration determination in the another mobile object 102 or driving unit 140 of the same type.

In yet another embodiment, the setting section 342 decides setting contents regarding rotation speed of the pump unit 270 (that is, rotation speed of the pump driving motor 274) for a case where the pump unit 270 is started for the purpose of determining the deterioration of the fluid 262. The setting section 342 may automatically change the setting contents regarding the rotation speed described above according to a predetermined algorithm. The setting section 342 may decide and/or change the setting contents regarding the rotation speed described above, based on (i) the operating frequency of the mobile object 102 or the driving unit 140, or (ii) the determination result of the deterioration determination in the another mobile object 102 or driving unit 140 of the same type.

In the present embodiment, the reading section 344 reads information indicating various measurement results (which may be referred to as measurement data) stored in the measurement data storage section 362. The reading section 344 will be described later in detail.

In the present embodiment, the decision section 346 decides whether to execute the deterioration determination. For example, the decision section 346 decides whether to execute the deterioration determination at fixed time intervals. The decision section 346 may decide whether to execute the deterioration determination. If specific conditions regarding a movement status of the mobile object 102 and/or a start status of the pump unit 270 are satisfied. The decision section 346 may decide whether to execute the deterioration determination at the fixed time intervals in a period in which the specific conditions regarding the movement status of the mobile object 102 and/or the start status of the pump unit 270 are satisfied. The decision section 346 will be described later in detail.

In the present embodiment, the determination section 348 acquires information indicating a value of the power index read by the reading section 344. The determination section 348 determines (i) whether the fluid has deteriorated, (ii) a degree of the deterioration of the fluid, and/or (iii) necessity of replacement of the fluid, based on the value of the power index described above. The decision section 346 will be described later in detail.

In the present embodiment, the measurement data storage section 362 stores various measurement data outputted by the measurement unit 150. The measurement data will be described later in detail.

In the present embodiment, the determination criterion storage section 364 stores information indicating various determination criteria to be used in the deterioration determination. The determination criterion will be described later in detail.

In the present embodiment, the determination model storage section 366 is included. A determination model to be used in the deterioration determination is stored. The determination model is generated by the management server 104, for example. The management server 104 may generate the determination model by machine learning by using a plurality of teaching data regarding a new fluid 262 and/or a plurality of teaching data regarding a deteriorated fluid 262.

In one embodiment, the determination model is generated by machine learning for determining (i) whether a transported fluid has deteriorated, (ii) a degree of deterioration of the transported fluid, and/or (iii) necessity of replacement of the transported fluid, from a value of a power index regarding a transport pump for transporting the transported fluid and a temperature of the transported fluid. In another embodiment, the determination model is generated by machine learning for determining (i) whether the transported fluid has deteriorated, (ii) the degree of the deterioration of the transported fluid, and/or (iii) the necessity of the replacement of the transported fluid, from the value of the power index regarding the transport pump for transporting the transported fluid, the temperature of the transported fluid, and a temperature of an environment in which the transported fluid is used.

Each of the plurality of teaching data regarding the new fluid 262 may be information in which a value of a liquid temperature of the fluid 262, the value of the power index at that liquid temperature, and a label indicating that the fluid is new are associated with one another. Each of the plurality of teaching data regarding the new fluid 262 may be information in which the value of the liquid temperature of the fluid 262, a value of an outside air temperature, the value of the power index at that liquid temperature and that outside air temperature, and the label indicating that the fluid is new are associated with one another.

Each of the plurality of teaching data regarding the deteriorated fluid 262 may be information in which the value of the liquid temperature of the fluid 262, the value of the power index at that liquid temperature, and a label indicating the deterioration or the degree of the deterioration are associated with one another. Each of the plurality of teaching data regarding the deteriorated fluid 262 may be information in which the value of the liquid temperature of the fluid 262, the value of the outside air temperature, the value of the power index at that liquid temperature and that outside air temperature, and the label indicating the deterioration or the degree of the deterioration are associated with one another.

The reading section 344 may be one example of a fluid temperature acquisition section, an environment temperature acquisition section, and/or a power index acquisition section. The decision section 346 may be one example of a decision section. The determination section 348 may be one example of a determination section.

Figure 4:
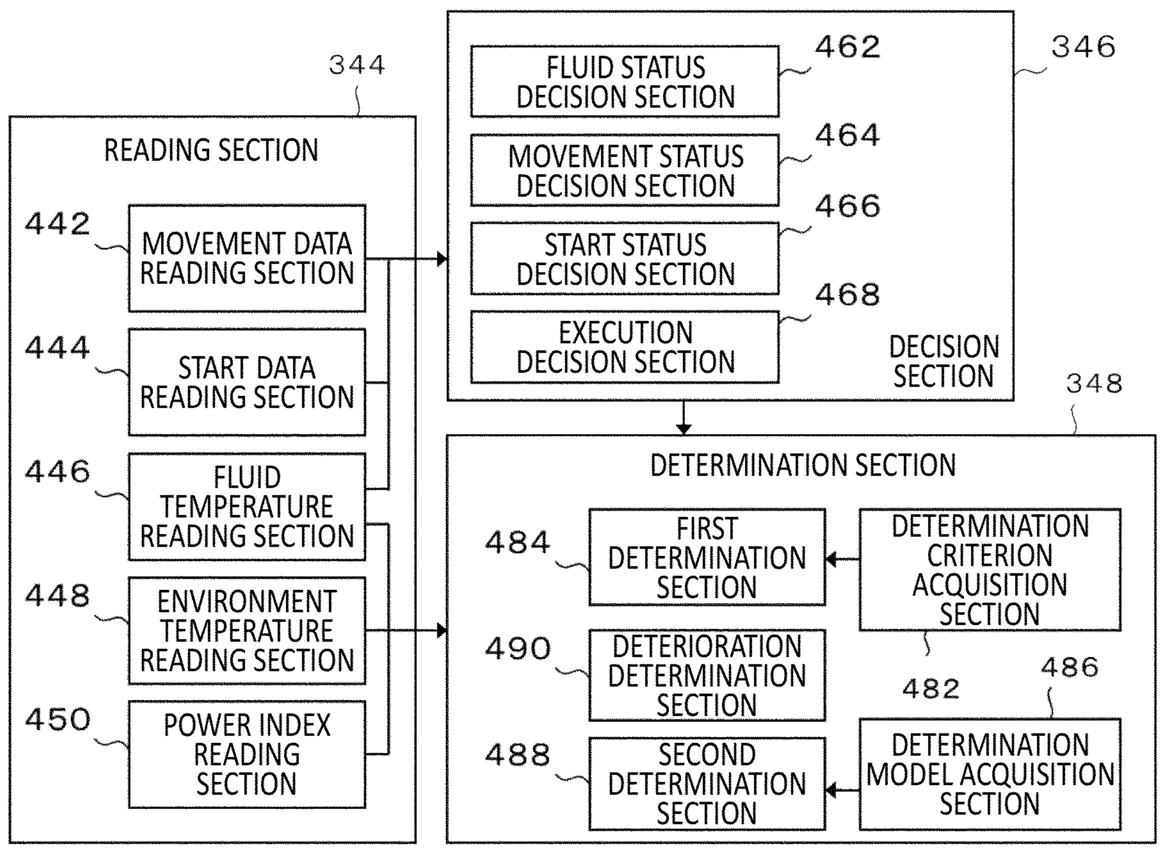
FIG. 4 schematically shows one example of an internal configuration of part of a deterioration management section 164.

FIG. 4 schematically shows one example of an internal configuration of part of the deterioration management section 164. FIG. 4 schematically shows examples of internal configurations of the reading section 344, the decision section 346, and the determination section 348.

In the present embodiment, the reading section 344 includes a movement data reading section 442, a start data reading section 444, a fluid temperature reading section 446, an environment temperature reading section 448, and a power index reading section 450, for example. In the present embodiment, the decision section 346 includes a fluid status decision section 462, a movement status decision section 464, a start status decision section 466, and an execution decision section 468, for example. In the present embodiment, the determination section 348 includes a determination criterion acquisition section 482 and a first determination section 484, for example. In the present embodiment, the determination section 348 includes a determination model acquisition section 486 and a second determination section 488, for example. In the present embodiment, the determination section 348 includes a deterioration determination section 490, for example.

In the present embodiment, the movement data reading section 442 reads data regarding a movement status of the mobile object 102 from the measurement data storage section 362, for example. In the present embodiment, the start data reading section 444 reads data regarding a start status of the pump unit 270 from the measurement data storage section 362, for example. The start data reading section 444 may read data regarding a start status of the pump driving motor 274.

In the present embodiment, the fluid temperature reading section 446 reads data regarding a temperature of the fluid 262 from the measurement data storage section 362, for example. The fluid temperature reading section 446 may read data regarding the temperature of the fluid in each of a plurality of sampling periods included in a determination period.

In the present embodiment, the environment temperature reading section 448 reads data regarding an outside air temperature from the measurement data storage section 362, for example. The fluid temperature reading section 446 may read the data regarding the outside air temperature in each of the plurality of sampling periods included in the determination period. If the outside air temperature is not used in determination processing of the determination section 348, the environment temperature reading section 448 does not need to read the data regarding the outside air temperature.

In the present embodiment, the power index reading section 450 reads data regarding a power index from the measurement data storage section 362, for example. The fluid temperature reading section 446 may read the data regarding the power index in each of the plurality of sampling periods included in the determination period.

The power index reading section 450 may read the data regarding the power index in each of at least two sampling periods of the plurality of sampling periods. The power index reading section 450 acquires information indicating the temperature of the fluid in an nth sampling period (n is an integer equal to or greater than 2.), at least if an absolute value of difference between the temperature of the fluid in the nth sampling period of the plurality of sampling periods and the temperature of the fluid in a sampling period in which determination regarding the power index was executed immediately before the nth sampling period meets a predetermined condition. If the absolute value of the difference described above does not meet the above predetermined condition, the power index reading section 450 does not need to acquire the information indicating the temperature of the fluid in the nth sampling period. The predetermined condition includes a condition that the absolute value is greater than a predetermined value, or a condition that the absolute value is equal to or greater than the predetermined value, for example.

More specifically, if the decision section 346 decides to execute the determination processing, the power index reading section 450 reads the data regarding the power index. On the other hand, if the decision section 346 decides not to execute the determination processing, the power index reading section 450 does not read the data regarding the power index.

The power index reading section 450 may read the data regarding the power index according to a setting decided by the setting section 342. For example, if the above setting stipulates that the power index is at least one of power consumption amount (Wh) of the pump in each sampling period, a statistic amount of power consumption (W) of the pump in each sampling period, or a statistic amount of torque (N·m) of the pump in each sampling period, the power index reading section 450 may acquire information indicating a value of the power index in each of one or more sampling periods.

The power index reading section 450 may read the data regarding the power index if rotation speed of the pump driving motor 274 is a predetermined value or falls within a predetermined numerical range. In this case, the power index may be at least one of power consumption amount (Wh) of the pump driving motor 274 in each sampling period, a statistic amount of power consumption (W) of the pump driving motor 274 in each sampling period, or a statistic amount of torque (N·m) of the pump driving motor 274 in each sampling period. This improves accuracy of deterioration determination. In addition, since there is no more need to read data regarding the rotation speed of the pump driving motor 274 as the power index, time required for the determination processing is shortened, and a load on a resource to be used for the determination processing is reduced.

In the present embodiment, the fluid status decision section 462 decides a status of temperature fluctuation of the fluid 262. For example, the fluid status decision section 462 decides whether the status of the temperature fluctuation of the fluid 262 meets a predetermined condition. The fluid status decision section 462 outputs, to the execution decision section 468, information indicating a decision result.

For example, in the nth sampling period (n is an integer equal to or greater than 2.) of the plurality of sampling periods, the fluid status decision section 462 first derives the absolute value of the difference between the temperature of the fluid in the nth sampling period and the temperature of the fluid in the sampling period in which the determination regarding the power index was executed immediately before the nth sampling period. Next, the fluid status decision section 462 decides whether the absolute value of the difference described above meets the predetermined condition. The predetermined condition includes the condition that the absolute value is greater than the predetermined value, or the condition that the absolute value is equal to or greater than the predetermined value, for example.

In the present embodiment, the movement status decision section 464 decides the movement status of the mobile object 102. For example, the movement status decision section 464 decides whether the movement status of the mobile object 102 meets a predetermined condition. The movement status decision section 464 outputs, to the execution decision section 468, information indicating a decision result.

For example, the movement status decision section 464 decides whether the movement status of the mobile object 102 meets the predetermined condition, based on at least one of movement velocity of the mobile object, a movement distance from a position where the user of the mobile object started the mobile object, or elapsed time from a time point where the user of the mobile object started the mobile object. The predetermined condition includes a condition that the movement distance and/or the elapsed time described above are greater than predetermined values and a condition that the mobile object 102 has stopped, for example. The condition that the mobile object 102 has stopped may be a condition that the movement velocity of the mobile object 102 is 0 km/h, or may be a condition that the movement velocity of the mobile object 102 is 0 km/h for a period having a predetermined length.

In the present embodiment, the start status decision section 466 decides the start status of the pump unit 270. For example, the start status decision section 466 decides whether the start status of the pump unit 270 meets a predetermined condition. The predetermined condition may be a condition for confirming that the pump unit 270 can be started in an oil deterioration determination mode. Examples of the predetermined condition include a condition that the pump unit 270 has not been started in a cooling/lubricating mode and/or a condition that the pump unit 270 is not out of order. The start status decision section 466 outputs, to the execution decision section 468, information indicating a decision result.

For example, the start status decision section 466 decides whether the start status of the pump unit 270 meets the predetermined condition, based on presence or absence of an instruction to start the pump unit 270 and/or a type of that instruction. Examples of the predetermined condition include a condition that the instruction to start the pump unit 270 has not been outputted, a condition that an instruction to start the pump unit 270 in the cooling/lubricating mode has not been outputted, a condition that an instruction indicating a failure of the pump unit 270 has not been outputted, and the like.

In the present embodiment, the execution decision section 468 decides whether the deterioration determination is executed by using measurement data for a specific period. The execution decision section 468 decides whether the above deterioration determination is executed, based on at least one of the status of the temperature fluctuation of the fluid 262 decided by the fluid status decision section 462, the movement status of the mobile object 102 decided by the movement status decision section 464, or the start status of the pump unit 270 decided by the start status decision section 466.

For example, if the temperature fluctuation is small, the execution decision section 468 decides that the deterioration determination is not executed. For example, if a length of the movement distance or a length of movement time of the mobile object 102 is smaller than a predetermined value, the execution decision section 468 decides that the deterioration determination is not executed. For example, if the mobile object 102 has not stopped, the execution decision section 468 decides that the deterioration determination is not executed. For example, if the instruction to start the pump unit 270 has been outputted, the execution decision section 468 decides that the deterioration determination is not executed.

The execution decision section 468 may decide, by deciding whether the determination processing in the first determination section 484 or the second determination section 488 is executed, whether the deterioration determination is executed, or may decide, by deciding whether the determination processing in the deterioration determination section 490 is executed, whether the deterioration determination is executed.

In one embodiment, if the absolute value of the difference between the temperature of the fluid in the nth sampling period (n is an integer equal to or greater than 2.) of the plurality of sampling periods and the temperature of the fluid in the sampling period in which the determination regarding the power index was executed immediately before the nth sampling period does not meet the predetermined condition, the execution decision section 468 may decide not to determine whether the value of the power index meets a criterion, or not to output information indicating whether the value of the power index meets the criterion, in the nth sampling period. If the execution decision section 468 decides not to output the information indicating whether the value of the power index meets the criterion, determination may be executed as to whether the value of the power index meets the criterion, or that determination may not be executed. The predetermined condition includes the condition that the absolute value is greater than the predetermined value, or the condition that the absolute value is equal to or greater than the predetermined value, for example.

In another embodiment, if an absolute value of difference between the temperature of the fluid in an (n−1)th sampling period (n is an integer equal to or greater than 2.) of the plurality of sampling periods and the temperature of the fluid in the nth sampling period of the plurality of sampling periods does not meet a predetermined condition, the execution decision section 468 may decide not to execute determination processing of deterioration, or not to output a determination result of that determination processing even if executing the determination processing of the deterioration. The predetermined condition includes the condition that the absolute value is greater than the predetermined value, or the condition that the absolute value is equal to or greater than the predetermined value, for example.

In the present embodiment, the determination criterion acquisition section 482 acquires information indicating a determination criterion to be used in the determination processing of the first determination section 484, in reference to the determination criterion storage section 364, for example. The determination criterion is a numerical range for which at least one of an upper limit or a lower limit is predetermined, or a numerical range to be derived based on a predetermined function, for example.

In one embodiment, the determination criterion storage section 364 may store information indicating one or more determination criteria respectively corresponding to one or more fluid temperature ranges which are one or more numerical ranges regarding the temperature of the fluid 262. The determination criterion storage section 364 acquires the information indicating the one or more determination criteria from the management server 104, for example. In this case, the determination criterion acquisition section 482 may decide a determination criterion (which may be referred to as an adaptive criterion) of the one or more determination criteria that corresponds to the temperature of the fluid 262 acquired by the fluid temperature reading section 446. The determination criterion acquisition section 482 may output, to the first determination section 484, the information indicating the determination criterion described above.

In another embodiment, the determination criterion storage section 364 may store the information indicating the one or more determination criteria respectively corresponding to one or more combinations of the one or more fluid temperature ranges which are the one or more numerical ranges regarding the temperature of the fluid 262 and one or more environment temperature ranges which are one or more numerical ranges regarding a temperature of an environment (for example, outside air temperature). The determination criterion storage section 364 acquires the information indicating the one or more determination criteria from the management server 104, for example. In this case, the determination criterion acquisition section 482 may decide, as the adaptive criterion, a determination criterion of the one or more determination criteria that corresponds to the temperature of the fluid 262 acquired by the fluid temperature reading section 446 and the outside air temperature acquired by the environment temperature reading section 448. The determination criterion acquisition section 482 may output, to the first determination section 484, the information indicating the determination criterion described above.

In the present embodiment, the first determination section 484 determines (i) whether the fluid has deteriorated, (ii) a degree of the deterioration of the fluid, and/or (iii) necessity of replacement of the fluid, based on whether the value of the power index acquired by the power index reading section 450 meets the determination criterion acquired by the determination criterion acquisition section 482. The first determination section 484 may determine (i) whether the fluid has deteriorated, (ii) the degree of the deterioration of the fluid, and/or (iii) the necessity of the replacement of the fluid, based on whether the value of the power index acquired by the power index reading section 450 meets the above adaptive criterion.

In the present embodiment, the first determination section 484 determines (i) whether the fluid has deteriorated, (ii) the degree of the deterioration of the fluid, and/or (iii) the necessity of the replacement of the fluid, in cooperation with the deterioration determination section 490. As mentioned above, the power index reading section 450 acquires the information indicating the value of the power index in each of the at least two sampling periods of the plurality of sampling periods. The first determination section 484 derives at least two determination results by determining whether the value of the power index in each of the at least two sampling periods meets the determination criterion or the adaptive criterion acquired by the determination criterion acquisition section 482 (which may be referred to as determination processing regarding a power index), for example. The first determination section 484 outputs, to the deterioration determination section 490, information indicating the at least two determination results. As will be described later, the deterioration determination section 490 determines (i) whether the fluid has deteriorated, (ii) the degree of the deterioration of the fluid, and/or (iii) the necessity of the replacement of the fluid, based on the at least two determination results outputted by the first determination section 484.

According to the present embodiment, the determination processing regarding the power index may be executed multiple times during a single determination period. This improves determination accuracy as compared with a case where the first determination section 484 determines the deterioration of the fluid based on a result of the determination processing regarding the power index at a single time point during the single determination period.

In the present embodiment, the determination model acquisition section 486 acquires a determination model to be used in the determination processing of the determination model acquisition section 486, in reference to the determination model storage section 366, for example. In one embodiment, the determination model acquisition section 486 acquires the determination model (which may be referred to as a first determination model) generated by machine learning for determining (i) whether a transported fluid has deteriorated, (ii) a degree of deterioration of the transported fluid, and/or (iii) necessity of replacement of the transported fluid, from the value of the power index regarding a transport pump for transporting the transported fluid. In another embodiment, the determination model acquisition section 486 acquires the determination model (which may be referred to as a second determination model) generated by the machine learning for determining (i) whether the transported fluid has deteriorated, (ii) the degree of the deterioration of the transported fluid, and/or (iii) the necessity of the replacement of the transported fluid, from the value of the power index regarding the transport pump for transporting the transported fluid, a temperature of the transported fluid, and a temperature of an environment in which the transported fluid is used.

In the present embodiment, the second determination section 488 outputs, by using the determination model acquired by the determination model acquisition section 486, information indicating (i) whether the fluid has deteriorated, (ii) the degree of the deterioration of the fluid, and/or (iii) the necessity of the replacement of the fluid, from the information indicating the value of the power index acquired by the power index acquisition section. In one embodiment, the second determination section 488 outputs, by using the first determination model, information indicating (i) whether the fluid 262 has deteriorated, (ii) a degree of the deterioration of the fluid 262, and/or (iii) necessity of replacement of the fluid 262, from the information indicating the value of the power index acquired by the power index reading section 450 and the information indicating the temperature of the fluid acquired by the fluid temperature reading section 446. In another embodiment, the second determination section 488 outputs, by using the second determination model, the information indicating (i) whether the fluid 262 has deteriorated, (ii) the degree of the deterioration of the fluid 262, and/or (iii) the necessity of the replacement of the fluid 262, from the information indicating the value of the power index acquired by the power index reading section 450, the information indicating the temperature of the fluid acquired by the fluid temperature reading section 446, and information indicating the outside air temperature acquired by the environment temperature reading section 448.

In the present embodiment, the second determination section 488 determines (i) whether the fluid has deteriorated, (ii) the degree of the deterioration of the fluid, and/or (iii) the necessity of the replacement of the fluid, in cooperation with the deterioration determination section 490. As mentioned above, the power index reading section 450 acquires the information indicating the value of the power index in each of the at least two sampling periods of the plurality of sampling periods. In this case, the second determination section 488 acquires an output result from the determination model as the determination result for each of the at least two sampling periods (which may be referred to as determination processing regarding a power index), for example. The second determination section 488 outputs, to the deterioration determination section 490, the information indicating the at least two determination results. As will be described later, the deterioration determination section 490 determines (i) whether the fluid has deteriorated, (ii) the degree of the deterioration of the fluid, and/or (iii) the necessity of the replacement of the fluid, based on the at least two determination results outputted by the second determination section 488.

According to the present embodiment, the determination processing regarding the power index may be executed multiple times during the single determination period. This improves the determination accuracy as compared with a case where the second determination section 488 determines the deterioration of the fluid based on the result of the determination processing regarding the power index at the single time point during the single determination period.

The deterioration determination section 490 outputs the information indicating (i) whether the fluid 262 has deteriorated, (ii) the degree of the deterioration of the fluid 262, and/or (iii) the necessity of the replacement of the fluid 262, based on the determination result of the first determination section 484 or the determination result of the second determination section 488. For example, as mentioned above, the power index reading section 450 acquires the information indicating the value of the power index in each of the at least two sampling periods of the plurality of sampling periods. In addition, the first determination section 484 and the second determination section 488 output the at least two determination results. The deterioration determination section 490 outputs the information indicating (i) whether the fluid 262 has deteriorated, (ii) the degree of the deterioration of the fluid 262, and/or (iii) the necessity of the replacement of the fluid 262, based on either one of the at least two determination results from the first determination section 484 or the at least two determination results from the second determination section 488. Processing of the deterioration determination section 490 will be described later in detail.

The fluid temperature reading section 446 may be one example of a fluid temperature acquisition section. The environment temperature reading section 448 may be one example of an environment temperature acquisition section. The power index reading section 450 may be one example of a power index acquisition section. The execution decision section 468 may be one example of a decision section. The first determination section 484 may be one example of a determination section. The second determination section 488 may be one example of a determination section. The deterioration determination section 490 may be one example of a determination section. The data regarding the power index may be one example of information indicating a value of a power index. Each sampling period may be one example of each period.

One Example of Another Embodiment

In the present embodiment, the determination section 348 has been described in detail, by taking as an example a case where the determination section 348 includes the determination criterion acquisition section 482, the first determination section 484, the determination model acquisition section 486, the second determination section 488, and the deterioration determination section 490. However, the determination section 348 is not limited to the present embodiment. Similarly, a procedure for determining (i) whether the fluid has deteriorated, (ii) the degree of the deterioration of the fluid, and/or (iii) the necessity of the replacement of the fluid based on the value of the power index is not limited to the present embodiment.

In another embodiment, the determination section 348 includes the first determination section 484 and the deterioration determination section 490. In the present embodiment, the determination section 348 may further include the determination criterion acquisition section 482. According to the present embodiment, (i) whether the fluid has deteriorated, (ii) the degree of the deterioration of the fluid, and/or (iii) the necessity of the replacement of the fluid are determined based on the value of the power index and a predetermined determination criterion.

In yet another embodiment, the determination section 348 includes the second determination section 488. In the present embodiment, the determination section 348 may further include at least one of the determination model acquisition section 486 and the deterioration determination section 490. According to the present embodiment, (i) whether the fluid has deteriorated, (ii) the degree of the deterioration of the fluid, and/or (iii) the necessity of the replacement of the fluid are determined based on the value of the power index and the determination model generated in advance by the machine learning. For example, when the value of the power index is inputted into the determination model, that determination model outputs the information indicating (i) whether the fluid has deteriorated, (ii) the degree of the deterioration of the fluid, and/or (iii) the necessity of the replacement of the fluid.

In the present embodiment, the deterioration management section 164 has been described in detail, by taking as an example a case where the first determination section 484 determines (i) whether the fluid has deteriorated, (ii) the degree of the deterioration of the fluid, and/or (iii) the necessity of the replacement of the fluid in cooperation with the deterioration determination section 490. Specifically, during the single determination period, the first determination section 484 executed the determination processing regarding the power index multiple times, and the deterioration determination section 490 determined the deterioration of the fluid based on a plurality of determination results regarding the power index. However, the deterioration management section 164 is not limited to the present embodiment.

In another embodiment, the first determination section 484 may output the result of the determination processing regarding the power index as a determination result regarding the deterioration of the fluid. In this case, the deterioration management section 164 does not need to include the deterioration determination section 490, and the first determination section 484 may have at least part of a function of the deterioration determination section 490.

In the present embodiment, the deterioration management section 164 has been described in detail, by taking as an example a case where the second determination section 488 determines (i) whether the fluid has deteriorated, (ii) the degree of the deterioration of the fluid, and/or (iii) the necessity of the replacement of the fluid in cooperation with the deterioration determination section 490. Specifically, during the single determination period, the second determination section 488 executed the determination processing regarding the power index multiple times, and the deterioration determination section 490 determined the deterioration of the fluid based on the plurality of determination results regarding the power index. However, the deterioration management section 164 is not limited to the present embodiment.

In another embodiment, the second determination section 488 may output the result of the determination processing regarding the power index as the determination result regarding the deterioration of the fluid. In this case, the deterioration management section 164 does not need to include the deterioration determination section 490, and the second determination section 488 may have the at least part of the function of the deterioration determination section 490.

FIG. 5 schematically shows one example of a data structure of a determination criterion regarding power index 500. The determination criterion 500 may be one example of one or more determination criteria to be stored in the determination criterion storage section 364. In the present embodiment, the determination criterion 500 stores, for each of temperature ranges 522 of one or more fluids 262, a determination criterion regarding power index 524 of the pump unit 270 at that temperature range.

As mentioned above, viscosity of the fluid 262 greatly varies depending on a temperature of the fluid 262. Therefore, defining a numerical range at normal time for each of the temperature ranges of the fluid 262 allows to determine precisely a status of the viscosity of the fluid 262 and a status of deterioration of the fluid 262. Note that the determination criterion storage section 364 may store the one or more determination criteria 500 respectively corresponding to one or more power indexes.

FIG. 6 schematically shows one example of a data structure of a determination criterion regarding power index 600. The determination criterion 600 may be one example of one or more determination criteria to be stored in the determination criterion storage section 364. In the present embodiment, the determination criterion 600 stores, for each combination of each of temperature ranges 622 of the one or more fluids 262 and each of one or more outside air temperature ranges 624, a determination criterion regarding power index 626 of the pump unit 270 in that combination. As mentioned above, viscosity of the fluid 262 greatly varies depending on a temperature of the fluid 262. In addition, the temperature of the fluid 262 is affected by an outside air temperature. Therefore, defining a numerical range at normal time for each of combinations of the temperature ranges of the fluid 262 and the outside air temperature ranges allows to determine more precisely a status of the viscosity of the fluid 262 and a status of deterioration of the fluid 262. Note that determination criterion storage section 364 may store one or more determination criteria 600 respectively corresponding to one or more power indexes.

Figure 7:
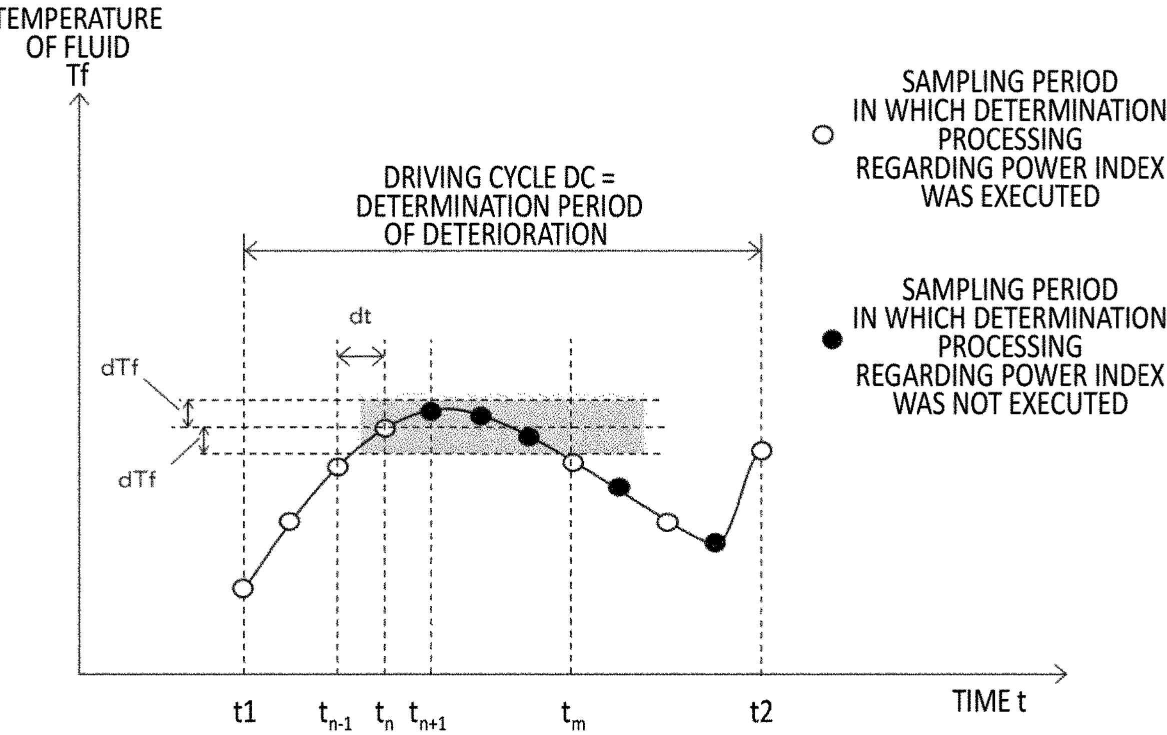
FIG. 7 schematically shows one example of execution timing of determination processing regarding a power index.

FIG. 7 schematically shows one example of execution timing of determination processing regarding a power index. The present embodiment schematically shows one example of the execution timing of the determination processing regarding the power index, by taking as an example a case where the determination processing regarding the deterioration is executed for each driving cycle. For example, the setting section 342 decides that a determination period of deterioration determination is a single driving cycle, so that the determination processing regarding the deterioration is executed for each driving cycle.

As mentioned above, the first determination section 484 or the second determination section 488 executes the determination processing regarding the power index multiple times during a single determination period. Specifically, the decision section 346 decides whether the determination processing regarding the power index is executed in each of a plurality of periods (which may be referred to as sampling periods) included in the single determination period. If the decision section 346 decides to execute the determination processing regarding the power index, the first determination section 484 or the second determination section 488 executes the determination processing regarding the power index. In the single determination period, time intervals dt of two adjacent sampling periods may be substantially the same or may be different.

As shown in FIG. 7, a plurality of sampling periods are included during a driving cycle from time t1 to time t2. In FIG. 7, white circles indicate sampling periods in which the determination processing regarding the power index is executed, and black circles indicate sampling periods in which the determination processing regarding the power index is not executed.

As mentioned above, the execution decision section 468 of the decision section 346 decides whether the determination processing regarding the power index is executed, based on at least one of a status of temperature fluctuation of the fluid 262 decided by the fluid status decision section 462, a movement status of the mobile object 102 decided by the movement status decision section 464, or a start status of the pump unit 270 decided by the start status decision section 466. Note that, as mentioned above, the execution decision section 468 may decide that information indicating whether a value of the power index meets a criterion is not outputted, instead of deciding whether the determination processing regarding the power index is executed.

In the embodiment described in connection to FIG. 7, the execution timing of the determination processing regarding the power index is described in detail, by taking as an example a case where the execution decision section 468 of the decision section 346 decides whether the determination processing regarding the power index is executed based on the status of the temperature fluctuation of the fluid 262 decided by the fluid status decision section 462. In the embodiment described in connection to FIG. 7, the execution timing of the determination processing regarding the power index is described in detail, by taking as an example a case where, when an absolute value of difference between a temperature of the fluid in an nth sampling period (n is an integer equal to or greater than 2.) of the plurality of sampling periods and the temperature of the fluid in a sampling period in which determination regarding the power index was executed immediately before the nth sampling period does not meet a predetermined condition, the execution decision section 468 decides that whether the value of the power index meets the criterion is not determined, in the nth sampling period. As mentioned above, the predetermined condition includes a condition that the absolute value is greater than a predetermined value, or a condition that the absolute value is equal to or greater than the predetermined value, for example.

As shown in FIG. 7, according to the present embodiment, commencement of an (n−1)th sampling period is time tn−1, commencement of the nth sampling period is time tn, commencement of an (n+1)th sampling period is time tn+1, and commencement of an mth sampling period is time tm. According to the present embodiment, the determination processing regarding the power index is executed in the (n−1)th sampling period, the nth sampling period, and the mth sampling period. On the other hand, in a period from an end of the nth sampling period to a start of the mth sampling period, the determination processing regarding the power index is not executed. Note that n is an integer equal to or greater than 2 and m is an integer greater than n.

According to the present embodiment, an absolute value of difference between a temperature Tn of the fluid 262 in the nth sampling period and a temperature Tn−1 of the fluid 262 in the (n−1)th sampling period is greater than a predetermined value dTf. Therefore, the determination processing regarding the power index is executed by using the value of the power index in the nth sampling period. This allows to presume a state of viscosity of the fluid 262 at the temperature Tn or in a temperature segment to which the temperature Tn belongs.

On the other hand, according to the present embodiment, an absolute value of difference between a temperature Tn+1 of the fluid 262 in the (n+1)th sampling period and the temperature Tn of the fluid 262 in the nth sampling period is smaller than the predetermined value dTf. Therefore, for the (n+1)th sampling period, the determination processing regarding the power index is not executed. This suppresses duplication of data.

Subsequently, at the time tm, an absolute value of difference between a temperature Tm of the fluid 262 in the mth sampling period and the temperature Tn of the fluid 262 in the nth sampling period is greater than the predetermined value dTf again. Therefore, the determination processing regarding the power index is executed by using the value of the power index in the mth sampling period. This allows to presume the state of the viscosity of the fluid 262 at the temperature Tm or in a temperature segment to which the temperature Tm belongs.

Figure 8:
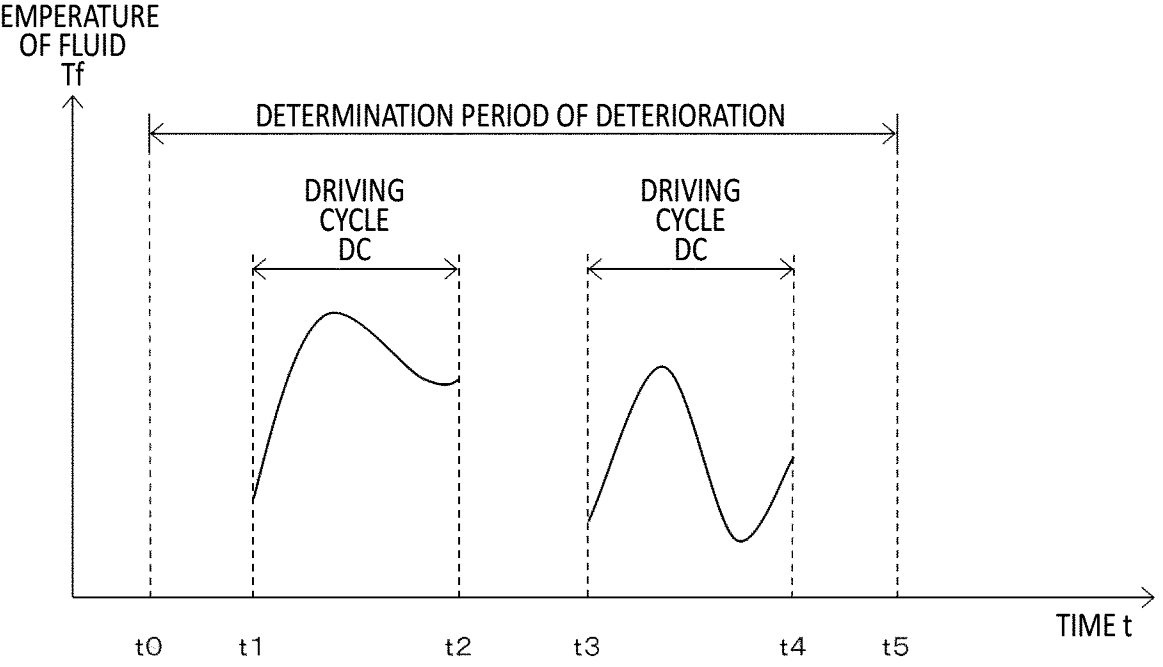
FIG. 8 schematically shows another example of a period in which determination processing regarding deterioration of a fluid is to take place.

FIG. 8 schematically shows another example of a period in which determination processing regarding deterioration of a fluid is to take place. The present embodiment schematically shows one example of execution timing of determination processing regarding a power index, by taking as an example a case where the determination processing regarding the deterioration is executed for each period having a predetermined length. For example, the setting section 342 decides a length of a determination period, so that the determination processing regarding the deterioration is executed for each period having the above length.

According to the present embodiment, a plurality of driving cycles may be included during the above period. According to the embodiment described in connection to FIG. 8, a driving cycle from time t1 to time t2 and a driving cycle from time t3 to time t4 are included during the determination period from time t0 to time t5. As described in connection to FIG. 7, a plurality of sampling periods are included during each driving cycle.

FIG. 9 schematically shows one example of a data structure of a measurement data 900. According to the present embodiment, the measurement data 900 includes a plurality of records. Each record of the measurement data 900 stores identification information of driving cycle 922, identification information of sampling period 924, measurement time 932, a measurement value 934 obtained by various sensors at each measurement time in association with one another, for example.

The measurement value 934 obtained by the various sensors includes a measurement value of a temperature of the fluid 262, a measurement value of rotation speed of the pump unit 270, and a measurement value of torque of the pump unit 270, for example. The measurement value 934 obtained by the various sensors may include a measurement value of an outside air temperature. The measurement value 934 obtained by the various sensors may include measurement values of power consumption and/or a power consumption amount of the pump unit 270, instead of the measurement values of the rotation speed and the torque of the pump unit 270, or in addition to the measurement values of the rotation speed and the torque of the pump unit 270.

FIG. 10 schematically shows one example of a data structure of a determination result of power index 1000. According to the present embodiment, the determination result 1000 includes a plurality of records. Each record of the determination result 1000 stores identification information of driving cycle 1022, identification information of sampling period 1024, a measurement result of power index 1032, a determination result of power index 1034 in association with one another, for example. The measurement result of power index 1032 may include a type of a power index and a value of that power index. As mentioned above, the determination result of power index 1034 stores information indicating a determination result by the first determination section 484 or the second determination section 488.

In FIG. 10, if the determination result of power index 1034 for a specific sampling period is OK, it is presumed that viscosity of the fluid 262 was normal in that period. On the other hand, if the determination result of power index 1034 for the specific sampling period is NG, it is presumed that the viscosity of the fluid 262 was not normal in that period. As mentioned above, according to the present embodiment, determination processing regarding the power index is executed multiple times during a determination period regarding deterioration. As a result, the deterioration of the fluid 262 is determined based on a statistic amount of a plurality of determination results obtained through the determination processing regarding the power index. This improves accuracy of deterioration determination. The deterioration determination will be described later in detail.

Figure 11:
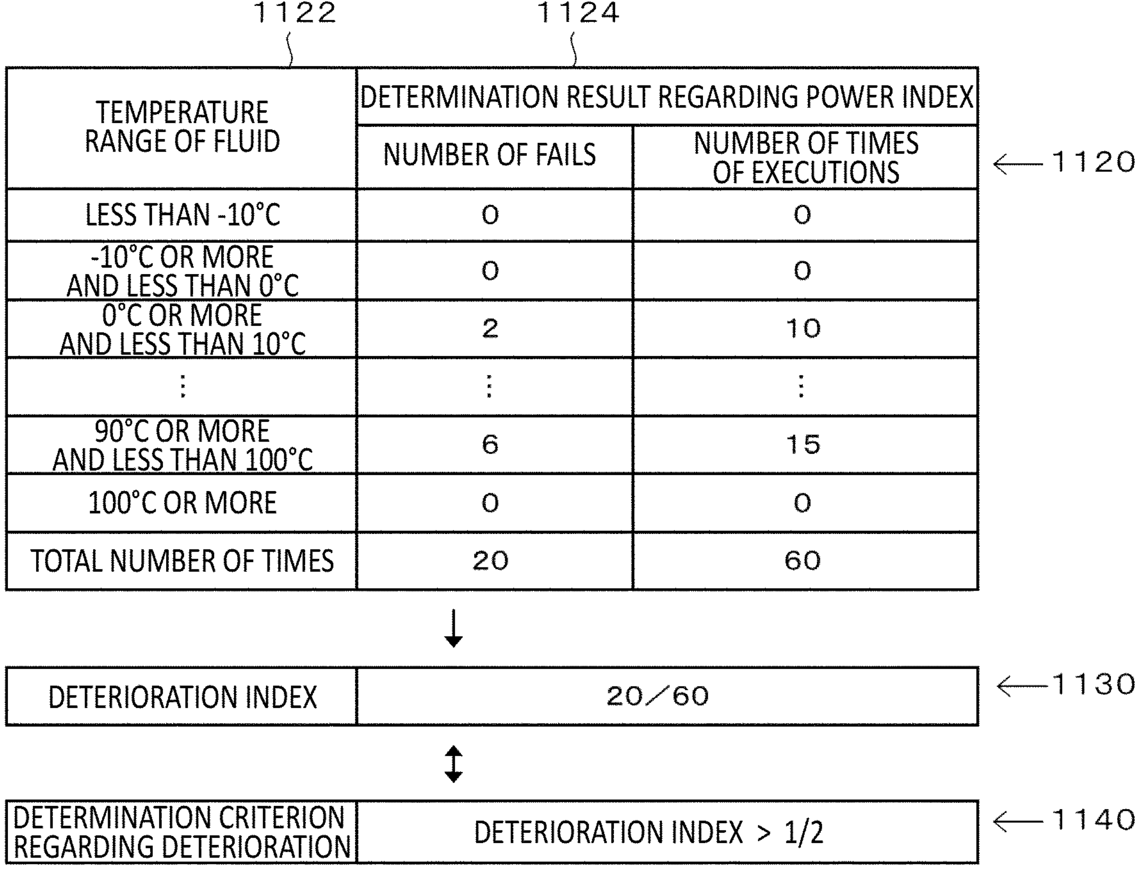
FIG. 11 schematically shows one example of a procedure for determining deterioration of a fluid from a determination result of power index.

FIG. 11 schematically shows one example of a procedure for determining deterioration of a fluid from a determination result of power index. According to the present embodiment, for example, first, the deterioration determination section 490 generates an aggregate result 1120 by classifying, according to predetermined temperature segment, a plurality of determination results obtained through determination processing regarding a power index. The aggregate result 1120 stores a fluid temperature range 1122 and a determination result of power index 1124 in association with each other, for example. In the present embodiment, the determination result of power index 1124 includes a cumulative value of the number of times that Fail has been outputted in the determination processing regarding the power index, and a cumulative value of the number of times that the determination processing regarding the power index has been executed, for example.

Next, the deterioration determination section 490 derives a value 1130 of an index representing the deterioration of the fluid 262 (which may be referred to as a deterioration index), based on the determination result of power index 1124 of the aggregate result 1120. For example, the deterioration determination section 490 derives, as the deterioration index, a ratio of the cumulative value of the number of times that Fail has been outputted, to the cumulative value of the number of times that the determination processing regarding the power index has been executed. Next, the deterioration determination section 490 determines whether the fluid 262 has deteriorated, by comparing the value of deterioration index 1130 and a determination criterion regarding deterioration 1140.

One Example of Another Embodiment

The present embodiment has described in detail a procedure for determining (i) whether the fluid has deteriorated, (ii) a degree of the deterioration of the fluid, and/or (iii) necessity of replacement of the fluid based on a value of the power index in each of a plurality of sampling periods included in a single determination period, by taking as an example a case where acquisition processing of the value of the power index, the determination processing regarding the power index, derivation processing of the deterioration index, and determination processing regarding the deterioration of the fluid are performed. However, the above procedure is not limited to the present embodiment.

According to another embodiment, the above procedure includes the determination processing regarding the power index and the determination processing regarding the deterioration of the fluid. The above procedure does not need to include the derivation processing of the deterioration index. In this case, for example, the second determination section 488 determines (i) whether the fluid has deteriorated, (ii) the degree of the deterioration of the fluid, and/or (iii) the necessity of the replacement of the fluid, based on the value of the power index in each of the plurality of sampling periods included in the single determination period, by utilizing a determination model generated by machine learning.

The deterioration determination section 490 may determine (i) whether the fluid has deteriorated, (ii) the degree of the deterioration of the fluid, and/or (iii) the necessity of the replacement of the fluid, based on the value of the power index in each of the plurality of sampling periods included in the single determination period, by utilizing the determination model generated by the machine learning. In one example, the deterioration determination section 490 outputs, by using the determination model generated by the machine learning for determining (i) whether the fluid has deteriorated, (ii) the degree of the deterioration of the fluid, and/or (iii) the necessity of the replacement of the fluid from the determination result regarding the power index, information indicating (i) whether the fluid has deteriorated, (ii) the degree of the deterioration of the fluid, and/or (iii) the necessity of the replacement of the fluid, from information indicating the determination result regarding the power index of the determination executed based on the value of the power index in each of the plurality of sampling periods included in the single determination period. In another example, the deterioration determination section 490 outputs, by using the determination model generated by the machine learning for determining (i) whether the fluid has deteriorated, (ii) the degree of the deterioration of the fluid, and/or (iii) the necessity of the replacement of the fluid from a temperature of the fluid and the determination result regarding the power index, the information indicating (i) whether the fluid has deteriorated, (ii) the degree of the deterioration of the fluid, and/or (iii) the necessity of the replacement of the fluid, from the information indicating the determination result regarding the power index of the determination executed based on the value of the power index in each of the plurality of sampling periods included in the single determination period and information indicating the temperature of the fluid in each sampling period.

Figure 12:
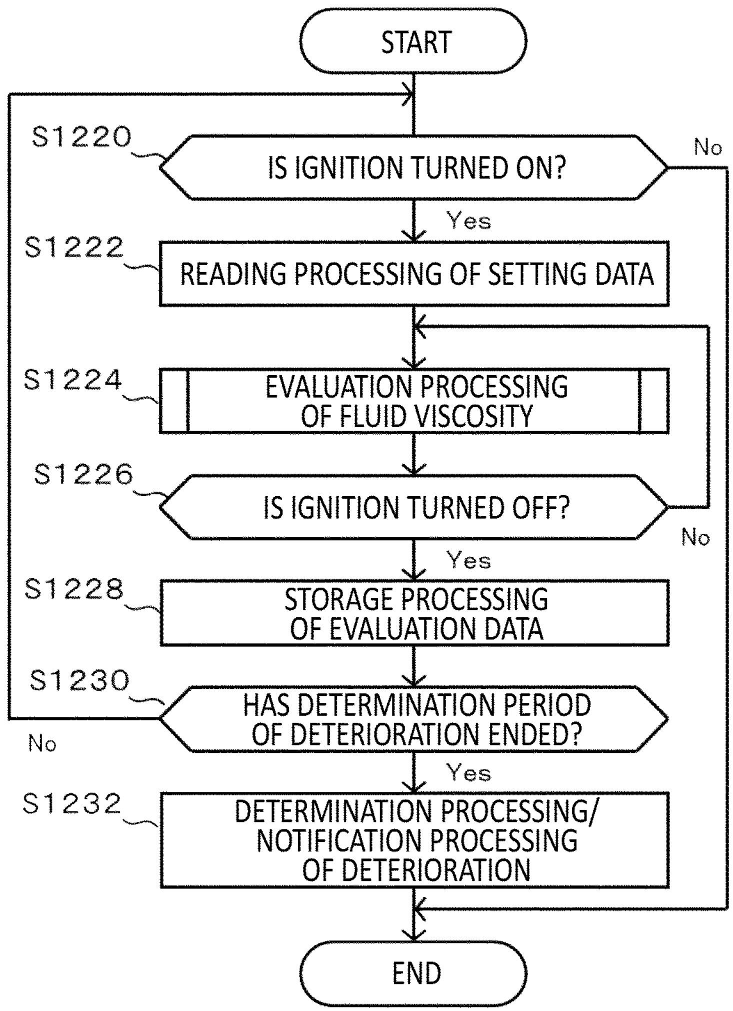
FIG. 12 schematically shows one example of information processing in the deterioration management section 164.

FIG. 12 schematically shows one example of information processing in the deterioration management section 164. According to the present embodiment, first, in Step 1220 (Step may be abbreviated as S), for example, the setting section 342 determines whether an ignition switch of the mobile object 102 is turned on. If the ignition switch of the mobile object 102 is not turned on (in case of No in Step 1220), the processing ends.

On the other hand, if the ignition switch of the mobile object 102 is turned on, in S1222, the setting section 342 reads various setting data regarding deterioration determination. This decides various setting contents regarding the deterioration determination. In addition, an initial value of a counter for counting the number of times that the determination processing regarding the power index mentioned above has been executed and an initial value of a counter for counting the number of times that Fail has been outputted are set.

Next, S1224 executes processing for evaluating whether viscosity of the fluid 262 is normal (which may be referred to as viscosity evaluation). Specifically, as mentioned above, in the first determination section 484 or the second determination section 488, the determination regarding the power index of the pump unit 270 is executed. The viscosity evaluation will be described later in detail.

Next, in S1226, for example, the deterioration determination section 490 determines whether the ignition switch of the mobile object 102 is turned off. If the ignition switch of the mobile object 102 is not turned off (in case of No in Step 1226), the processing of S1224 is repeated. The processing of S1224 may be periodically repeated. On the other hand, if the ignition switch of the mobile object 102 is turned off, in S1228, data indicating a result of the viscosity evaluation (which may be referred to as evaluation data) in S1224 is stored in the storage section 166. For example, the deterioration determination section 490 updates a content of the aggregate result 1120 based on the determination result 1000 generated in S1224.

Next, S1230, for example, the deterioration determination section 490 determines whether determination period of deterioration has ended. If it is determined that the determination period of the deterioration has not ended (in case of No in S1230), the processing of S1220 to S1228 is repeated. On the other hand, if it is determined that the determination period of the deterioration has ended (in case of Yes in S1230), in S1232, the deterioration determination section 490 determines (i) whether the fluid 262 has deteriorated, (ii) a degree of the deterioration of the fluid 262, and/or (iii) necessity of replacement of the fluid 262. For example, the deterioration determination section 490 derives the value of deterioration index 1130 based on the aggregate result 1120. In addition, the deterioration determination section 490 determines (i) whether the fluid 262 has deteriorated, (ii) the degree of the deterioration of the fluid 262, and/or (iii) the necessity of the replacement of the fluid 262, by comparing the value of deterioration index 1130 and the determination criterion regarding deterioration 1140.

In S1232, the deterioration management section 164 transmits, to the management server 104, information indicating a determination result regarding the deterioration of the fluid 262. In addition, in S1232, a result of determination processing regarding the deterioration of the fluid 262 is notified to the user 20 and/or the maintenance company 40. The above notification may be transmitted from the mobile object 102 to the communication terminal 22 and/or the communication terminal 42, or may be transmitted from the management server 104 to the communication terminal 22 and/or the communication terminal 42. As a result, the processing ends.

Figure 13:
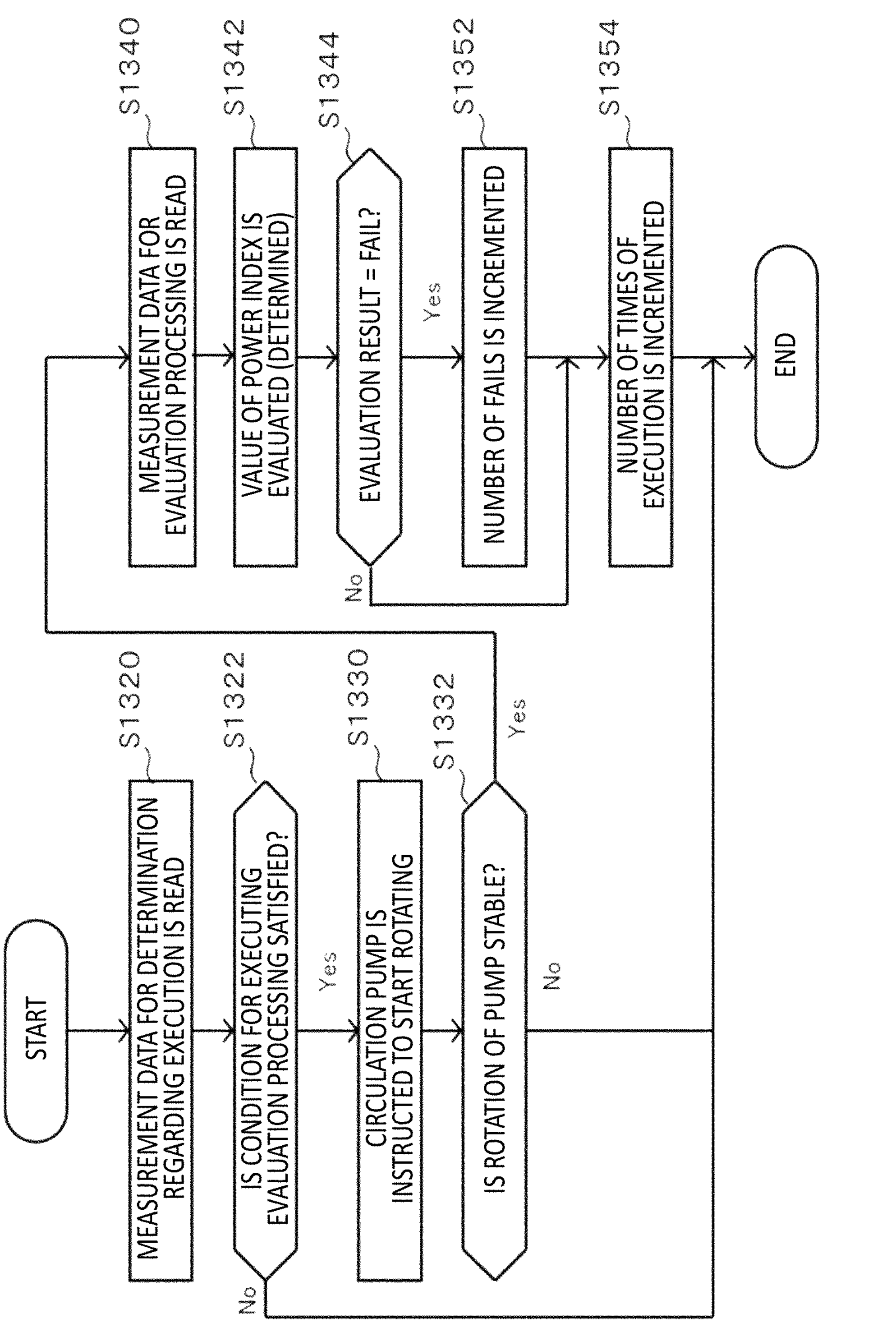
FIG. 13 schematically shows one example of evaluation processing of fluid viscosity.

FIG. 13 schematically shows one example of evaluation processing of fluid viscosity in S1224 described in connection to FIG. 12. According to the present embodiment, when a current sampling period has come, first, in 51320, the reading section 344 reads measurement data to be used for determination processing regarding execution in decision section 346, in reference to the measurement data storage section 362. For example, the reading section 344 reads temperature data of the fluid 262 in the current sampling period and temperature data of the fluid 262 in a sampling period in which determination regarding a power index was executed immediately before. In addition, the reading section 344 reads data regarding a movement status of the mobile object 102 and data regarding a start status of the pump unit 270.

Next, the decision section 346 decides whether the determination regarding the power index (which may be referred to as evaluation of viscosity of a fluid) is executed in the current sampling period. Specifically, the decision section 346 decides whether a condition for executing the determination regarding the power index is satisfied. If it is decided that the above condition is not satisfied (in case of No in S1322), the processing ends.

On the other hand, if it is decided that the above condition is satisfied (in case of Yes in S1322), in 51330, the pump control section 326 instructs the pump unit 270 to start. As a result, the circulation pump 272 starts to rotate. Next, in S1332, the pump control section 326 determines whether the rotation of the circulation pump 272 is stable. If it is determined that the rotation of the circulation pump 272 is not stable (in case of No in S1332), the processing ends.

On the other hand, if it is determined that the rotation of the circulation pump 272 is stable (in case of Yes in S1332), in 51340, the reading section 344 reads measurement data to be used for determination processing regarding the power index in the determination section 348, in reference to the measurement data storage section 362. In one embodiment, if the determination section 348 executes the determination processing by using the first determination section 484, the determination criterion acquisition section 482 acquires an appropriate determination criterion. In another embodiment, if the determination section 348 executes the determination processing by using the second determination section 488, the determination model acquisition section 486 acquires the appropriate determination model.

Next, in 51342, the determination section 348 determines a value of the power index in the current sampling period. If a determination result is Fail (in case of Yes in S1344), in 51352, the determination section 348 increments the number of Fails corresponding to a temperature range to which a temperature of a current fluid 262 belongs, in the determination result 1000. In addition, in 51354, the determination section 348 increments the number of times of execution corresponding to the temperature range to which the temperature of the current fluid 262 belongs, in the determination result 1000. On the other hand, if the determination result is not Fail (in case of No in S1344), in 51354, the determination section 348 increments the number of times of execution corresponding to the temperature range to which the temperature of the current fluid 262 belongs, in the determination result 1000. As a result, the processing ends.

Figure 14:
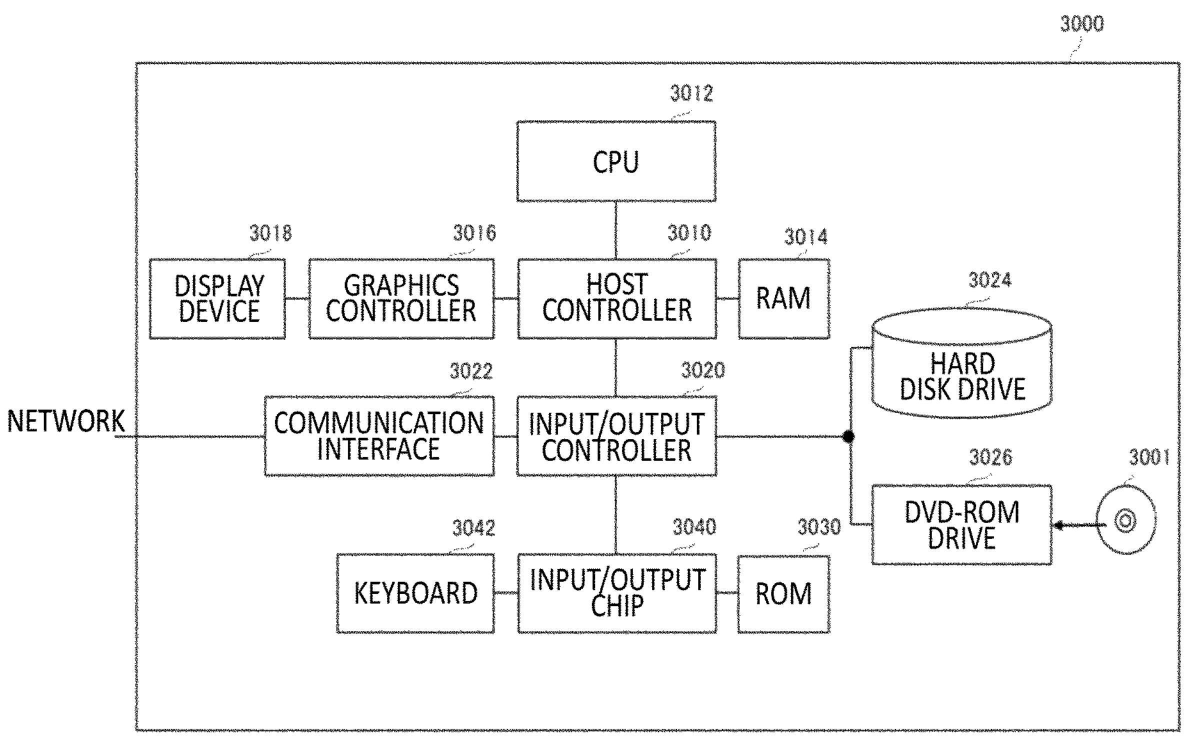
FIG. 14 schematically shows one example of an internal configuration of a computer 3000.

FIG. 14 shows an example of a computer 3000 in which a plurality of embodiments of the present invention may be entirely or partially embodied. For example, at least part of the mobile object 102 is realized by the computer 3000. For example, at least part of the control unit 160 is realized by the computer 3000. For example, at least part of the management server 104 is realized by the computer 3000.

A program that is installed in the computer 3000 can cause the computer 3000 to perform an operation correlated to an apparatus according to the embodiment of the present invention or to function as one or more "units" of the apparatus, or cause the computer 3000 to perform the operation or the one or more units thereof, and/or cause the computer 3000 to perform processes according to the embodiment of the present invention or steps thereof. Such a program may be performed by the CPU 3012 to cause the computer 3000 to perform particular operations correlated to some or all of the blocks of flowcharts and block diagrams described herein.

The computer 3000 in accordance with the present embodiment includes a CPU 3012, a RAM 3014, a graphics processing unit (GPU) 3016, and a display device 3018, which are mutually connected by a host controller 3010. The computer 3000 also includes an input/output unit such as a communication interface 3022, a hard disk drive 3024, a DVD-ROM drive 3026, and an IC card drive, which are connected to the host controller 3010 via the input/output controller 3020. The computer also includes legacy input/output units such as a ROM 3030 and a keyboard 3042, which are connected to the input/output controller 3020 via an input/output chip 3040.

The CPU 3012 operates according to programs stored in the ROM 3030 and the RAM 3014, thereby controlling each unit. The GPU 3016 acquires image data generated by the CPU 3012 on a frame buffer or the like provided in the RAM 3014 or in itself, and causes the image data to be displayed on a display device 3018.

The communication interface 3022 communicates with other electronic devices via a network. The hard disk drive 3024 stores programs and data that are used by the CPU 3012 within the computer 3000. The DVD-ROM drive 3026 reads the programs or the data from the DVD-ROM 3001, and provides the hard disk drive 3024 with the programs or the data via the RAM 3014. The IC card drive reads programs and data from an IC card and/or writes programs and data into the IC card.

The ROM 3030 stores therein a boot program or the like that is performed by the computer 3000 at the time of activation, and/or a program depending on the hardware of the computer 3000. The input/output chip 3040 may also connect various input/output units to the input/output controller 3020 via a parallel port, a serial port, a keyboard port, a mouse port or the like.

A program is provided by a computer-readable storage medium, such as the DVD-ROM 3001 or the IC card. The program is read from the computer-readable storage medium, installed into the hard disk drive 3024, RAM 3014, or ROM 3030, which are also examples of computer-readable storage medium, and performed by the CPU 3012. The information processing described in these programs is read into the computer 3000, resulting in cooperation between a program and the above described various types of hardware resources. An apparatus or method may be constituted by realizing the operation or processing of information in accordance with the usage of the computer 3000.

For example, when communication is performed between the computer 3000 and an external device, the CPU 3012 may perform a communication program loaded onto the RAM 3014 to instruct communication processing to the communication interface 3022, based on the processing described in the communication program. The communication interface 3022, under the control of the CPU 3012, reads the transmission data stored in the transmission buffer region provided in the recording medium such as RAM 3014, hard disk drive 3024, DVD-ROM 3001, or IC card, and transmits the read transmission data to the network or writes the reception data received from the network to the reception buffer region or the like provided on the recording medium.

In addition, the CPU 3012 may cause all or a necessary portion of a file or a database to be read into the RAM 3014, the file or the database having been stored in an external recording medium such as the hard disk drive 3024, the DVD-ROM drive 3026 (DVD-ROM 3001), the IC card, etc., and perform various types of processing on the data on the RAM 3014. The CPU 3012 may then write back the processed data to the external recording medium.

Various types of information such as various types of programs, data, tables, and databases may be stored in a recording medium and subjected to information processing. The CPU 3012 may perform various types of processing on the data read from the RAM 3014, which includes various types of operations, information processing, condition judging, conditional branch, unconditional branch, search/replacement of information, or the like, etc., as described throughout this disclosure and designated by a command sequence of programs, and writes the result back to the RAM 3014. In addition, the CPU 3012 may search for information in a file, a database, etc., in the recording medium. For example, when a plurality of entries, each having an attribute value of a first attribute correlated to an attribute value of a second attribute, are stored in the recording medium, the CPU 3012 may search for an entry whose attribute value of the first attribute matches the condition a designated condition, from among the plurality of entries, and read the attribute value of the second attribute stored in the entry, thereby obtaining the attribute value of the second attribute correlated to the first attribute satisfying the predetermined condition.

The above described program or software modules may be stored in the computer-readable storage medium on or near the computer 3000. In addition, a recording medium such as a hard disk or a RAM provided in a server system connected to a dedicated communication network or the Internet can be used as the computer-readable storage medium, thereby providing the program to the computer 3000 via the network.

While the embodiments of the present invention have been described, the technical scope of the present invention is not limited to the above embodiments. It is apparent to persons skilled in the art that various alterations or improvements can be made to the above embodiments. It is also apparent from the description of the claims that the embodiments to which such alterations or improvements are made can be included in the technical scope of the present invention.

Note that the operations, procedures, steps, stages, and the like of each processing performed by an apparatus, system, program, and method shown in the claims, embodiments, or diagrams can be realized in any order as long as the order is not indicated by "prior to," "before," or the like and as long as the output from a previous processing is not used in a later processing. Even if the operational flow is described by using phrases such as "first" or "next" in the claims, embodiments, or diagrams, it does not necessarily mean that the processing must be executed in this order.

EXPLANATION OF REFERENCES

10: communication network; 20: user; 22: communication terminal; 40: maintenance company; 42: communication terminal; 100: management system; 102: mobile object; 104: management server; 120: input/output unit; 130: thrust generation unit; 140: driving unit; 150: measurement unit; 160: control unit; 162: control section; 164: deterioration management section; 166: storage section; 252: body driving motor; 254: gearbox; 256: shaft; 260: oil pan; 262: fluid; 270: pump unit; 272: circulation pump; 274: pump driving motor; 280: flow channel; 292: liquid temperature sensor; 294: outside air temperature sensor; 296: power system sensor; 298: circulatory system sensor; 322: input/output control section; 324: overall control section; 326: pump control section; 342: setting section; 344: reading section; 346: decision section; 348: determination section; 362: measurement data storage section; 364: determination criterion storage section; 366: determination model storage section; 442: movement data reading section; 444: start data reading section; 446: fluid temperature reading section; 448: environment temperature reading section; 450: power index reading section; 462: fluid status decision section; 464: movement status decision section; 466: start status decision section; 468: execution decision section; 482: determination criterion acquisition section; 484: first determination section; 486: determination model acquisition section; 488: second determination section; 490: deterioration determination section; 500: determination criterion; 522: temperature range; 524: determination criterion; 600: determination criterion; 622: temperature range; 624: temperature range; 626: determination criterion; 900: measurement data; 922: identification information; 924: identification information; 932: measurement time; 934: measurement value; 1000: determination result; 1022: identification information; 1024: identification information; 1032: measurement result; 1034: determination result; 1120: aggregate result; 1122: temperature range; 1124: determination result;

1130: value; 1140: determination criterion; 3000: computer; 3001: DVD-ROM; 3010: host controller; 3012: CPU; 3014: RAM; 3016: GPU; 3018: display device; 3020: input/output controller; 3022: communication interface; 3024: hard disk drive; 3026: DVD-ROM drive; 3030: ROM; 3040: input/output chip; and 3042: keyboard.

What is claimed is:

1. A mobile object, comprising:

a driving unit configured to output driving force for moving the mobile object;

a fluid containing, as a principal component, a lubricant agent to be used for lubricating a machine component constituting at least part of the driving unit;

a pump; and a determination apparatus configured to determine deterioration of the fluid to be used in circulation, the determination apparatus comprising:

at least one processor;

a power index acquisition section that uses the at least one processor to acquire information indicating a value of a power index, which is an index that represents a state of the pump for circulating the fluid and is correlated with magnitude of power consumption of the pump; and a determination section that uses the at least one processor to, based on the value of the power index, determine (i) whether the fluid has deteriorated, (ii) a degree of the deterioration of the fluid, and/or (iii) necessity of replacement of the fluid, wherein the determination section is configured to, based on whether the value of the power index acquired by the power index acquisition section meets a predetermined determination criterion, determine (i) whether the fluid has deteriorated, (ii) the degree of the deterioration of the fluid, and/or (iii) the necessity of the replacement of the fluid, and the determination criterion is a numerical range for which at least one of an upper limit or a lower limit is predetermined, or a numerical range to be derived based on a predetermined function, the determination apparatus further comprising a fluid temperature acquisition section that uses the at least one processor to acquire information indicating a temperature of the fluid, wherein the determination section is configured to:

acquire information indicating one or more determination criteria including the determination criterion that respectively correspond to one or more fluid temperature ranges which are one or more numerical ranges regarding the temperature of the fluid;

decide an adaptive criterion which is a determination criterion of the one or more determination criteria that corresponds to the temperature of the fluid acquired by the fluid temperature acquisition section; and determine (i) whether the fluid has deteriorated, (ii) the degree of the deterioration of the fluid, and/or (iii) the necessity of the replacement of the fluid, based on whether the value of the power index acquired by the power index acquisition section meets the adaptive criterion, wherein the determination apparatus further comprises a decision section that uses the at least one processor to, based on at least one of a movement status of the mobile object or a start status of the pump, decide whether to execute determination processing of the deterioration of the fluid.

2. The mobile object according to claim 1, wherein the fluid temperature acquisition section is configured to acquire the information indicating the temperature of the fluid in each of a plurality of sampling periods included in a determination period in which determination processing of the deterioration of the fluid is to take place, the power index acquisition section is configured to acquire the information indicating the value of the power index in each of at least two sampling periods of the plurality of sampling periods, and the determination section is configured to:

derive at least two determination results by determining whether the value of the power index in each of the at least two sampling periods meets the adaptive criterion; and determine (i) whether the fluid has deteriorated, (ii) the degree of the deterioration of the fluid, and/or (iii) the necessity of the replacement of the fluid, based on the at least two determination results.

3. The mobile object according to claim 2, wherein the power index acquisition section is configured to, at least if an absolute value of difference between the temperature of the fluid in an nth sampling period (n is an integer equal to or greater than 2.) of the plurality of sampling periods and the temperature of the fluid in a sampling period in which the determination regarding the power index was executed immediately before the nth sampling period meets a predetermined condition, acquire the information indicating the temperature of the fluid in the nth sampling period, and the predetermined condition includes a condition that the absolute value is greater than a predetermined value, or a condition that the absolute value is equal to or greater than a predetermined value.

4. The mobile object according to claim 2, further comprising a decision section that uses the at least one processor to decide whether to execute the determination processing of the deterioration of the fluid, wherein the decision section is configured to, if an absolute value of difference between the temperature of the fluid in an nth sampling period (n is an integer equal to or greater than 2.) of the plurality of sampling periods and the temperature of the fluid in a sampling period in which the determination regarding the power index was executed immediately before the nth sampling period does not meet a predetermined condition, decide not to determine whether the value of the power index meets the adaptive criterion, or not to output information indicating whether the value of the power index meets the adaptive criterion, in the nth sampling period, and the predetermined condition includes a condition that the absolute value is greater than a predetermined value, or a condition that the absolute value is equal to or greater than a predetermined value.

5. The mobile object according to claim 1, further comprising an environment temperature acquisition section that uses the at least one processor to acquire information indicating a temperature of an environment in which the fluid is used, wherein the determination section is configured to:

acquire information indicating the one or more determination criteria respectively corresponding to one or more combinations of the one or more fluid temperature ranges and one or more environment temperature ranges which are one or more numerical ranges regarding the temperature of the environment; and decide, as the adaptive criterion, a determination criterion of the one or more determination criteria that corresponds to the temperature of the fluid acquired by the fluid temperature acquisition section and the temperature of the environment acquired by the environment temperature acquisition section.

6. A mobile object, comprising:

a driving unit configured to output driving force for moving the mobile object;

a fluid containing, as a principal component, a lubricant agent to be used for lubricating a machine component constituting at least part of the driving unit;

a pump; and a determination apparatus configured to determine deterioration of the fluid to be used in circulation, the determination apparatus comprising:

at least one processor;

a power index acquisition section that uses the at least one processor to acquire information indicating a value of a power index, which is an index that represents a state of the pump for circulating the fluid and is correlated with magnitude of power consumption of the pump; and a determination section that uses the at least one processor to, based on the value of the power index, determine (i) whether the fluid has deteriorated, (ii) a degree of the deterioration of the fluid, and/or (iii) necessity of replacement of the fluid, wherein the determination section is configured to, by using a determination model generated by machine learning for determining (i) whether a transported fluid has deteriorated, (ii) a degree of deterioration of the transported fluid, and/or (iii) necessity of replacement of the transported fluid, from the value of the power index regarding a transport pump for transporting the transported fluid, output information indicating (i) whether the fluid has deteriorated, (ii) the degree of the deterioration of the fluid, and/or (iii) the necessity of the replacement of the fluid, from the information indicating the value of the power index acquired by the power index acquisition section, the determination apparatus further comprises:

a fluid temperature acquisition section that uses the at least one processor to acquire information indicating a temperature of the fluid in each of a plurality of sampling periods included in a determination period in which determination processing of the deterioration of the fluid is to take place; and a decision section that uses the at least one processor to decide whether to execute the determination processing of the deterioration of the fluid, wherein the decision section is configured to, if an absolute value of difference between the temperature of the fluid in an (n−1)th sampling period (n is an integer equal to or greater than 2.) of the plurality of sampling periods and the temperature of the fluid in an nth sampling period of the plurality of sampling periods does not meet a predetermined condition, decide not to execute the determination processing, or not to output a determination result of the determination processing even if executing the determination processing, and the predetermined condition includes a condition that the absolute value is greater than a predetermined value, or a condition that the absolute value is equal to or greater than a predetermined value.

* * * * *